United States Patent
Protopsaltis et al.

(10) Patent No.: US 11,730,608 B2
(45) Date of Patent: Aug. 22, 2023

(54) MONOBLOCK EXPANDABLE INTERBODY IMPLANT

(71) Applicant: Warsaw Orthopedic, Inc., Warsaw, IN (US)

(72) Inventors: Dimitri K. Protopsaltis, Memphis, TN (US); John A. Hall, Germantown, TN (US); Julien J. Prevost, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 106 days.

(21) Appl. No.: 17/373,903

(22) Filed: Jul. 13, 2021

(65) Prior Publication Data

US 2023/0018019 A1  Jan. 19, 2023

(51) Int. Cl.
*A61F 2/44* (2006.01)
*A61F 2/30* (2006.01)

(52) U.S. Cl.
CPC ...... *A61F 2/447* (2013.01); *A61F 2002/3054* (2013.01); *A61F 2002/30136* (2013.01);
(Continued)

(58) Field of Classification Search
CPC .. A61F 2/44; A61F 2/442; A61F 2/447; A61F 2002/30136; A61F 2002/30433;
(Continued)

(56) References Cited

U.S. PATENT DOCUMENTS

| 4,401,112 A | 8/1983 | Rezaian |
| 4,553,273 A | 11/1985 | Wu |

(Continued)

FOREIGN PATENT DOCUMENTS

| DE | 44 16 605 C1 | 6/1995 |
| EP | 0 767 636 A1 | 4/1997 |

(Continued)

OTHER PUBLICATIONS

International Search Report, and Written Opinion for Application. No. PCT/US2019/019067, dated Jun. 3, 2019.
(Continued)

*Primary Examiner* — Jessica Weiss
(74) *Attorney, Agent, or Firm* — Fox Rothschild LLP; P. Marshall Ticer

(57) ABSTRACT

A unibody implant movable between an expanded position and a contracted position is disclosed. The unibody implant may include a unitary expandable body defined by an inferior portion and a superior portion that are connected together. In various embodiments, a set screw may be rotatably supported by the body and configured to move a plug having a first inclined surface facing the distal side. In various embodiments, the set screw may be movable in the longitudinal direction towards the distal side upon rotation of the set screw along the rotation axis, for example. In various embodiments, movement of the set screw urges the plug against the superior portion thereby expanding a vertical distance between the superior and inferior sides of the body. In some embodiments, the plug may include a stabilizing element configured to transfer compressive forces between the superior portion and inferior portion.

20 Claims, 14 Drawing Sheets

(52) U.S. Cl.
CPC ............... *A61F 2002/30433* (2013.01); *A61F 2002/30579* (2013.01); *A61F 2002/30774* (2013.01)

(58) Field of Classification Search
CPC .... A61F 2002/3054; A61F 2002/30579; A61F 2002/30774
USPC .......................................... 623/17.11–17.16
See application file for complete search history.

(56) References Cited

U.S. PATENT DOCUMENTS

| | | | |
|---|---|---|---|
| 4,636,217 A | 1/1987 | Ogilvie et al. | |
| 4,759,769 A | 7/1988 | Hedman et al. | |
| 5,059,193 A | 10/1991 | Kuslich | |
| 5,171,278 A | 12/1992 | Pisharodi | |
| 5,336,223 A | 8/1994 | Rogers | |
| 5,390,683 A | 2/1995 | Pisharodi | |
| 5,522,899 A | 6/1996 | Michelson | |
| 5,554,191 A | 9/1996 | Lahille et al. | |
| 5,575,790 A | 11/1996 | Chen et al. | |
| 5,609,635 A | 3/1997 | Michelson | |
| 5,653,762 A | 8/1997 | Pisharodi | |
| 5,658,336 A | 8/1997 | Pisharodi | |
| 5,665,122 A | 9/1997 | Kambin | |
| 5,693,100 A | 12/1997 | Pisharodi | |
| 5,697,977 A | 12/1997 | Pisharodi | |
| 5,702,391 A | 12/1997 | Lin | |
| 5,702,453 A | 12/1997 | Rabbe et al. | |
| 5,702,455 A | 12/1997 | Saggar | |
| 5,800,550 A | 9/1998 | Sertich | |
| 5,865,848 A | 2/1999 | Baker | |
| 5,893,890 A | 4/1999 | Pisharodi | |
| 5,931,777 A | 8/1999 | Sava | |
| 5,980,522 A | 11/1999 | Koros et al. | |
| 6,045,579 A | 4/2000 | Hochshuler et al. | |
| 6,074,343 A | 6/2000 | Nathanson et al. | |
| 6,080,193 A | 6/2000 | Hochshuler et al. | |
| 6,099,531 A | 8/2000 | Bonutti | |
| 6,102,949 A | 8/2000 | Biedermann et al. | |
| 6,102,950 A | 8/2000 | Vaccaro | |
| 6,106,557 A | 8/2000 | Robioneck et al. | |
| 6,113,638 A | 9/2000 | Williams et al. | |
| 6,117,174 A | 9/2000 | Nolan | |
| 6,132,465 A | 10/2000 | Ray et al. | |
| 6,159,211 A | 12/2000 | Boriani et al. | |
| 6,159,244 A | 12/2000 | Suddaby | |
| 6,176,882 B1 | 1/2001 | Biedermann et al. | |
| 6,179,873 B1 | 1/2001 | Zientek | |
| 6,190,414 B1 | 2/2001 | Young et al. | |
| 6,193,757 B1 | 2/2001 | Foley et al. | |
| 6,217,579 B1 | 4/2001 | Koros | |
| 6,245,108 B1 | 6/2001 | Biscup | |
| 6,309,421 B1 | 10/2001 | Pisharodi | |
| 6,342,074 B1 | 1/2002 | Simpson | |
| 6,371,989 B1 | 4/2002 | Chauvin et al. | |
| 6,395,031 B1 | 5/2002 | Foley et al. | |
| 6,423,063 B1 | 7/2002 | Bonutti | |
| 6,432,106 B1 | 8/2002 | Fraser | |
| 6,436,140 B1 | 8/2002 | Liu et al. | |
| 6,443,989 B1 | 9/2002 | Jackson | |
| 6,443,990 B1 | 9/2002 | Aebi et al. | |
| 6,454,806 B1 | 9/2002 | Cohen et al. | |
| 6,454,807 B1 | 9/2002 | Jackson | |
| 6,461,359 B1 | 10/2002 | Tribus et al. | |
| 6,471,724 B2 * | 10/2002 | Zdeblick | A61B 1/3135 623/17.11 |
| 6,491,724 B1 | 12/2002 | Ferree | |
| 6,520,991 B2 | 2/2003 | Huene | |
| 6,520,993 B2 | 2/2003 | James et al. | |
| 6,527,803 B1 | 3/2003 | Crozet et al. | |
| 6,562,074 B2 | 5/2003 | Gerbec et al. | |
| 6,576,016 B1 | 6/2003 | Hochshuler et al. | |
| 6,623,525 B2 | 9/2003 | Ralph et al. | |
| 6,629,998 B1 | 10/2003 | Lin | |
| 6,635,086 B2 | 10/2003 | Lin | |
| 6,648,917 B2 | 11/2003 | Gerbec et al. | |
| 6,676,703 B2 | 1/2004 | Biscup | |
| 6,685,742 B1 | 2/2004 | Jackson | |
| 6,723,126 B1 | 4/2004 | Berry | |
| 6,770,096 B2 | 8/2004 | Bolger et al. | |
| 6,773,460 B2 | 8/2004 | Jackson | |
| 6,821,298 B1 | 11/2004 | Jackson | |
| 6,835,206 B2 | 12/2004 | Jackson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,923,814 B1 | 8/2005 | Hildebrand et al. | |
| 6,926,737 B2 | 8/2005 | Jackson | |
| 6,953,477 B2 | 10/2005 | Berry | |
| 6,955,691 B2 * | 10/2005 | Chae | A61F 2/447 623/17.11 |
| 6,964,687 B1 | 11/2005 | Bernard et al. | |
| 6,974,480 B2 | 12/2005 | Messerli et al. | |
| 6,984,234 B2 | 1/2006 | Bray | |
| 7,112,222 B2 | 9/2006 | Fraser et al. | |
| 7,135,043 B2 | 11/2006 | Nakahara et al. | |
| 7,137,997 B2 | 11/2006 | Paul | |
| 7,172,627 B2 | 2/2007 | Fiere et al. | |
| 7,204,853 B2 | 4/2007 | Gordon et al. | |
| 7,232,464 B2 | 6/2007 | Mathieu et al. | |
| 7,238,203 B2 | 7/2007 | Bagga et al. | |
| 7,316,714 B2 | 1/2008 | Gordon et al. | |
| 7,407,483 B2 | 8/2008 | Perez-Cruet et al. | |
| 7,481,766 B2 | 1/2009 | Lee et al. | |
| 7,491,168 B2 | 2/2009 | Raymond et al. | |
| 7,537,565 B2 | 5/2009 | Bass | |
| 7,618,456 B2 | 11/2009 | Mathieu et al. | |
| 7,625,394 B2 | 12/2009 | Molz, IV et al. | |
| 7,655,046 B2 | 2/2010 | Dryer et al. | |
| 7,678,148 B2 * | 3/2010 | Peterman | A61F 2/4455 623/17.11 |
| 7,703,727 B2 | 4/2010 | Selness | |
| 7,708,778 B2 | 5/2010 | Gordon et al. | |
| 7,708,779 B2 | 5/2010 | Edie et al. | |
| 7,727,280 B2 | 6/2010 | McLuen | |
| 7,753,958 B2 | 7/2010 | Gordon et al. | |
| 7,780,594 B2 | 8/2010 | Hutton | |
| 7,806,932 B2 | 10/2010 | Webb et al. | |
| 7,815,682 B1 | 10/2010 | Peterson et al. | |
| 7,819,801 B2 | 10/2010 | Miles et al. | |
| 7,828,849 B2 | 11/2010 | Lim | |
| 7,846,167 B2 | 12/2010 | Garcia et al. | |
| 7,846,207 B2 | 12/2010 | Lechmann et al. | |
| 7,850,731 B2 | 12/2010 | Brittan et al. | |
| 7,850,733 B2 | 12/2010 | Baynham et al. | |
| 7,862,616 B2 | 1/2011 | Lechmann et al. | |
| 7,875,076 B2 | 1/2011 | Mathieu et al. | |
| 7,892,173 B2 | 2/2011 | Miles et al. | |
| 7,909,869 B2 | 3/2011 | Gordon et al. | |
| 7,914,559 B2 | 3/2011 | Carls et al. | |
| 7,967,821 B2 | 6/2011 | Sicvol et al. | |
| 7,981,031 B2 | 7/2011 | Frasier et al. | |
| 8,016,836 B2 | 9/2011 | Corrao et al. | |
| 8,062,375 B2 | 11/2011 | Glerum et al. | |
| 8,105,382 B2 | 1/2012 | Olmos et al. | |
| 8,118,870 B2 | 2/2012 | Gordon et al. | |
| 8,118,871 B2 | 2/2012 | Gordon et al. | |
| 8,123,810 B2 | 2/2012 | Gordon et al. | |
| 8,147,550 B2 | 4/2012 | Gordon et al. | |
| 8,172,903 B2 | 5/2012 | Gordon et al. | |
| 8,182,539 B2 | 5/2012 | Tyber et al. | |
| 8,257,442 B2 | 9/2012 | Edie et al. | |
| 8,262,570 B2 | 9/2012 | White et al. | |
| 8,262,662 B2 | 9/2012 | Beardsley et al. | |
| 8,287,597 B1 | 10/2012 | Pimenta et al. | |
| 8,303,498 B2 | 11/2012 | Miles et al. | |
| 8,303,658 B2 | 11/2012 | Peterman | |
| 8,303,663 B2 | 11/2012 | Jimenez et al. | |
| 8,317,866 B2 | 11/2012 | Palmatier et al. | |
| 8,323,185 B2 | 12/2012 | Perez-Cruet et al. | |
| 8,328,872 B2 | 12/2012 | Duffield et al. | |
| 8,343,048 B2 | 1/2013 | Warren, Jr. | |
| 8,353,826 B2 | 1/2013 | Weiman | |

(56) References Cited

U.S. PATENT DOCUMENTS

| | | |
|---|---|---|
| 8,355,780 B2 | 1/2013 | Miles et al. |
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,506,635 B2 | 8/2013 | Palmatier et al. |
| 8,517,935 B2 | 8/2013 | Marchek et al. |
| 8,518,120 B2 | 8/2013 | Glerum et al. |
| 8,535,380 B2 | 9/2013 | Greenhalgh et al. |
| 8,550,994 B2 | 10/2013 | Miles et al. |
| 8,556,808 B2 | 10/2013 | Miles et al. |
| 8,556,979 B2 | 10/2013 | Glerum et al. |
| 8,579,809 B2 | 11/2013 | Parker |
| 8,579,979 B2 | 11/2013 | Edie et al. |
| 8,579,981 B2 | 11/2013 | Lim et al. |
| 8,602,984 B2 | 12/2013 | Raymond et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,715 B2 | 3/2014 | Sandhu |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,353 B2 | 5/2014 | Bagga et al. |
| 8,740,983 B1 | 6/2014 | Arnold et al. |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 | 9/2014 | Donahoe et al. |
| 8,845,731 B2 | 9/2014 | Weiman |
| 8,845,732 B2 | 9/2014 | Weiman |
| 8,845,734 B2 | 9/2014 | Weiman |
| 8,852,282 B2 | 10/2014 | Farley et al. |
| 8,864,833 B2 | 10/2014 | Glerum et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,343 B2 | 6/2016 | Duffield et al. |
| 9,370,434 B2 | 6/2016 | Weiman |
| 9,370,435 B2 | 6/2016 | Walkenhorst et al. |
| 9,381,008 B2 | 7/2016 | Thornburg |
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Arnin |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,468,405 B2 | 10/2016 | Miles et al. |
| 9,474,622 B2 | 10/2016 | McLaughlin et al. |
| 9,474,625 B2 | 10/2016 | Weiman |
| 9,480,573 B2 | 11/2016 | Perloff et al. |
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |
| 9,510,954 B2 | 12/2016 | Glerum et al. |
| 9,522,070 B2 | 12/2016 | Flower et al. |
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |

(56) References Cited

U.S. PATENT DOCUMENTS

| | | |
|---|---|---|
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |
| 9,585,767 B2 | 3/2017 | Robinson |
| 9,592,129 B2 | 3/2017 | Slivka et al. |
| 9,597,195 B2 | 3/2017 | Cain |
| 9,603,713 B2 | 3/2017 | Moskowitz et al. |
| 9,603,717 B2 | 3/2017 | Ibarra et al. |
| 9,615,818 B2 | 4/2017 | Baudouin et al. |
| 9,615,936 B2 | 4/2017 | Duffield et al. |
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Arnin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,907,671 B2 | 3/2018 | Fessler |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,943,342 B2 | 4/2018 | Tanaka et al. |
| 9,943,418 B2 | 4/2018 | Davenport et al. |
| 9,949,841 B2 | 4/2018 | Glerum et al. |
| 9,956,087 B2 | 5/2018 | Seifert et al. |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,016,282 B2 | 7/2018 | Seifert et al. |
| 10,016,284 B2 | 7/2018 | Moskowitz et al. |
| 10,022,239 B1 | 7/2018 | Lentner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,772 B2 | 7/2018 | Glerum et al. |
| 10,034,773 B2 | 7/2018 | McLaughlin et al. |
| 10,039,539 B2 | 8/2018 | Friedrich et al. |
| 10,039,650 B2 | 8/2018 | Lamborne et al. |
| 10,052,214 B2 | 8/2018 | Jimenez et al. |
| 10,060,469 B2 | 8/2018 | Jimenez et al. |
| 10,070,852 B2 | 9/2018 | Mast et al. |
| 10,076,320 B2 | 9/2018 | Mast et al. |
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |
| 10,111,758 B2 | 10/2018 | Robinson |
| 10,117,754 B2 | 11/2018 | Davenport et al. |
| 10,117,755 B2 | 11/2018 | Emerick et al. |
| 10,137,002 B2 | 11/2018 | Padovani et al. |
| 10,137,006 B2 | 11/2018 | Dewey et al. |
| 10,137,007 B2 | 11/2018 | Dewey et al. |
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,515 B2 | 1/2019 | Lee et al. |
| 10,172,652 B2 | 1/2019 | Woolley et al. |
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |

(56) References Cited

U.S. PATENT DOCUMENTS

| | | |
|---|---|---|
| 10,238,375 B2 | 3/2019 | O'Connell et al. |
| 10,238,383 B2 | 3/2019 | Moskowitz et al. |
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |
| 10,327,912 B1 | 6/2019 | Suddaby |
| 10,327,917 B2 | 6/2019 | Glerum et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,633 B2 | 10/2019 | Moskowitz et al. |
| 10,426,634 B1 | 10/2019 | Al-Jazaeri et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,960 B2 | 3/2020 | Duffield et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,166 B2 | 5/2020 | Weiman et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Weiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 | 11/2020 | Weiman et al. |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,523 B2 | 12/2020 | Weiman et al. |
| 10,874,524 B2 | 12/2020 | Bjork |
| 11,510,788 B2* | 11/2022 | Eisen .................. A61F 2/4425 |
| 2002/0045943 A1* | 4/2002 | Uk .......................... A61F 2/446 623/17.16 |
| 2002/0045945 A1* | 4/2002 | Liu .......................... A61F 2/446 623/17.16 |
| 2002/0116066 A1 | 8/2002 | Chauvin et al. |
| 2002/0128713 A1 | 9/2002 | Ferree |
| 2002/0151976 A1 | 10/2002 | Foley et al. |
| 2003/0050701 A1 | 3/2003 | Michelson |
| 2003/0130739 A1 | 7/2003 | Gerbec et al. |
| 2004/0172134 A1 | 9/2004 | Berry |
| 2004/0186570 A1 | 9/2004 | Rapp |
| 2004/0193158 A1 | 9/2004 | Lim et al. |
| 2004/0249461 A1 | 12/2004 | Ferree |
| 2004/0254643 A1 | 12/2004 | Jackson |
| 2004/0254644 A1 | 12/2004 | Taylor |
| 2005/0015149 A1 | 1/2005 | Michelson |
| 2005/0033429 A1 | 2/2005 | Kuo |
| 2005/0033439 A1 | 2/2005 | Gordon et al. |
| 2006/0122701 A1 | 6/2006 | Kiester |
| 2006/0129244 A1 | 6/2006 | Ensign |
| 2009/0024158 A1 | 1/2009 | Viker |
| 2009/0292361 A1 | 11/2009 | Lopez |
| 2010/0082109 A1 | 4/2010 | Greenhalgh et al. |
| 2010/0191336 A1 | 7/2010 | Greenhalgh |
| 2010/0211176 A1 | 8/2010 | Greenhalgh |
| 2011/0118843 A1 | 5/2011 | Mathieu et al. |
| 2011/0130838 A1 | 6/2011 | Morgenstern Lopez |
| 2011/0218572 A1 | 9/2011 | Lechmann et al. |
| 2011/0282396 A1* | 11/2011 | Shimko ................ A61C 8/0033 606/303 |
| 2012/0101581 A1 | 4/2012 | Mathieu et al. |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0197401 A1 | 8/2012 | Duncan et al. |
| 2012/0209385 A1 | 8/2012 | Aferzon |
| 2012/0215316 A1 | 8/2012 | Mohr et al. |
| 2013/0013070 A1* | 1/2013 | McCormack ........ A61B 17/863 623/17.16 |
| 2013/0190876 A1 | 7/2013 | Drochner et al. |
| 2013/0231747 A1 | 9/2013 | Olmos et al. |
| 2013/0317312 A1 | 11/2013 | Eastlack et al. |
| 2014/0107790 A1 | 4/2014 | Combrowski |
| 2014/0114420 A1 | 4/2014 | Robinson |
| 2014/0148904 A1* | 5/2014 | Robinson .............. A61F 2/447 623/17.16 |
| 2014/0163682 A1 | 6/2014 | Iott et al. |
| 2014/0180419 A1 | 6/2014 | Dmuschewsky |
| 2014/0194992 A1 | 7/2014 | Medina |

(56) References Cited

U.S. PATENT DOCUMENTS

| | | |
|---|---|---|
| 2014/0277500 A1 | 9/2014 | Logan et al. |
| 2015/0142114 A1* | 5/2015 | Pisharodi ............... A61F 2/4611 623/17.16 |
| 2015/0223945 A1 | 8/2015 | Weiman et al. |
| 2015/0230931 A1 | 8/2015 | Greenhalgh |
| 2016/0008924 A1 | 1/2016 | Canourgues et al. |
| 2016/0022434 A1* | 1/2016 | Robinson ............... A61F 2/4611 623/17.16 |
| 2016/0081681 A1 | 3/2016 | Waugh et al. |
| 2016/0089247 A1 | 3/2016 | Nichols et al. |
| 2016/0095710 A1 | 4/2016 | Juszczyk et al. |
| 2016/0242930 A1 | 8/2016 | Duffield et al. |
| 2016/0256291 A1 | 9/2016 | Miller |
| 2016/0296340 A1 | 10/2016 | Gordon et al. |
| 2016/0310291 A1 | 10/2016 | Greenhalgh |
| 2016/0345952 A1 | 12/2016 | Kucharzyk et al. |
| 2016/0367377 A1 | 12/2016 | Faulhaber |
| 2017/0010025 A1 | 1/2017 | Mayershofer |
| 2017/0029635 A1 | 2/2017 | Doll et al. |
| 2017/0035406 A1 | 2/2017 | Abidin et al. |
| 2017/0049651 A1 | 2/2017 | Lim et al. |
| 2017/0049653 A1 | 2/2017 | Lim et al. |
| 2017/0095345 A1 | 4/2017 | Davenport et al. |
| 2017/0100255 A1 | 4/2017 | Hleihil et al. |
| 2017/0100257 A1 | 4/2017 | Weiman et al. |
| 2017/0105844 A1 | 4/2017 | Kuyler et al. |
| 2017/0151065 A1 | 6/2017 | Warren et al. |
| 2017/0156882 A1 | 6/2017 | Rathbun et al. |
| 2017/0156884 A1 | 6/2017 | Rathbun et al. |
| 2017/0202678 A1 | 7/2017 | Duffield et al. |
| 2017/0215856 A1 | 8/2017 | Martinelli et al. |
| 2017/0224502 A1 | 8/2017 | Wolters et al. |
| 2017/0246006 A1 | 8/2017 | Carnes et al. |
| 2017/0290677 A1 | 10/2017 | Olmos et al. |
| 2017/0296352 A1 | 10/2017 | Richerme et al. |
| 2017/0367842 A1 | 12/2017 | Predick et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0030362 A1 | 2/2018 | Kosler et al. |
| 2018/0031810 A1 | 2/2018 | Hsu et al. |
| 2018/0036136 A1 | 2/2018 | Duffield et al. |
| 2018/0036138 A1 | 2/2018 | Robinson |
| 2018/0116891 A1 | 5/2018 | Beale et al. |
| 2018/0193164 A1 | 7/2018 | Shoshtaev |
| 2018/0206999 A1 | 7/2018 | Suddaby |
| 2018/0256356 A1 | 9/2018 | Robinson et al. |
| 2018/0256359 A1 | 9/2018 | Greenhalgh |
| 2018/0256360 A1 | 9/2018 | Cain |
| 2018/0256362 A1 | 9/2018 | Slivka et al. |
| 2018/0263784 A1 | 9/2018 | Bechtel et al. |
| 2018/0280142 A1 | 10/2018 | Schultz et al. |
| 2018/0303473 A1 | 10/2018 | Spann et al. |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1 | 11/2018 | Engstrom |
| 2018/0318102 A1 | 11/2018 | Seifert et al. |
| 2018/0338838 A1 | 11/2018 | Cryder et al. |
| 2018/0338841 A1 | 11/2018 | Miller et al. |
| 2018/0344307 A1 | 12/2018 | Hynes et al. |
| 2018/0360616 A1 | 12/2018 | Luu |
| 2019/0000640 A1 | 1/2019 | Weiman |
| 2019/0000702 A1 | 1/2019 | Lim et al. |
| 2019/0000707 A1 | 1/2019 | Lim et al. |
| 2019/0020121 A1 | 1/2019 | Paulotto et al. |
| 2019/0021716 A1 | 1/2019 | Waugh et al. |
| 2019/0021873 A1 | 1/2019 | Dmuschewsky |
| 2019/0046329 A1 | 2/2019 | Padovani et al. |
| 2019/0046381 A1 | 2/2019 | Lim et al. |
| 2019/0046383 A1 | 2/2019 | Lim et al. |
| 2019/0060083 A1 | 2/2019 | Weiman et al. |
| 2019/0082949 A1 | 3/2019 | Weiman |
| 2019/0083081 A1 | 3/2019 | Ortiz et al. |
| 2019/0091033 A1 | 3/2019 | Dewey et al. |
| 2019/0105175 A1 | 4/2019 | Zappacosta et al. |
| 2019/0125328 A1 | 5/2019 | Blain |
| 2019/0133434 A1 | 5/2019 | Lee et al. |
| 2019/0133645 A1 | 5/2019 | Gordon et al. |
| 2019/0133780 A1 | 5/2019 | Matthews et al. |
| 2019/0133784 A1 | 5/2019 | Gunn et al. |
| 2019/0133788 A1 | 5/2019 | Weiman et al. |
| 2019/0142480 A1 | 5/2019 | Woolley et al. |
| 2019/0151115 A1 | 5/2019 | Nichols et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0209155 A1 | 7/2019 | Mast et al. |
| 2019/0216453 A1 | 7/2019 | Predick et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0254650 A1 | 8/2019 | Martinelli et al. |
| 2019/0254838 A1 | 8/2019 | Miller et al. |
| 2019/0254839 A1 | 8/2019 | Nichols et al. |
| 2019/0262139 A1 | 8/2019 | Wolters |
| 2019/0269521 A1 | 9/2019 | Shoshtaev |
| 2019/0274670 A1 | 9/2019 | O'Connell et al. |
| 2019/0274671 A1 | 9/2019 | Lauf et al. |
| 2019/0274836 A1 | 9/2019 | Eisen et al. |
| 2019/0282373 A1 | 9/2019 | Alheidt |
| 2019/0290446 A1 | 9/2019 | Masson et al. |
| 2019/0290447 A1 | 9/2019 | Stein |
| 2019/0298524 A1 | 10/2019 | Lauf et al. |
| 2019/0298540 A1 | 10/2019 | Aghayev et al. |
| 2019/0321022 A1 | 10/2019 | Karpowicz et al. |
| 2019/0321190 A1 | 10/2019 | Wagner et al. |
| 2019/0328540 A1 | 10/2019 | Seifert et al. |
| 2019/0336301 A1 | 11/2019 | Engstrom |
| 2019/0336304 A1 | 11/2019 | Burkhardt et al. |
| 2019/0350573 A1 | 11/2019 | Vogel et al. |
| 2019/0358049 A1 | 11/2019 | Faulhaber |
| 2019/0358050 A1 | 11/2019 | Fessler |
| 2019/0358051 A1 | 11/2019 | Flower et al. |
| 2019/0388232 A1 | 12/2019 | Purcell et al. |
| 2020/0008951 A1 | 1/2020 | McClintock et al. |
| 2020/0030114 A1 | 1/2020 | Cain |
| 2020/0030116 A1 | 1/2020 | Jimenez et al. |
| 2020/0038200 A1 | 2/2020 | Foley et al. |
| 2020/0054461 A1 | 2/2020 | Marrocco et al. |
| 2020/0060844 A1 | 2/2020 | Mathieu et al. |
| 2020/0078190 A1 | 3/2020 | Rogers et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0129306 A1 | 4/2020 | Miller et al. |
| 2020/0129307 A1 | 4/2020 | Hunziker et al. |
| 2020/0138591 A1 | 5/2020 | Moskowitz et al. |
| 2020/0138593 A1 | 5/2020 | Martynova et al. |
| 2020/0146840 A1 | 5/2020 | Black et al. |
| 2020/0205993 A1 | 7/2020 | Davenport et al. |
| 2020/0222202 A1 | 7/2020 | Kuyler et al. |
| 2020/0229944 A1 | 7/2020 | Suh et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0289287 A1 | 9/2020 | Emerick et al. |
| 2020/0297507 A1 | 9/2020 | Iott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390565 A1 | 12/2020 | Jimenez et al. |
| 2020/0397593 A1 | 12/2020 | Davenport et al. |

(56) References Cited

U.S. PATENT DOCUMENTS

| | | |
|---|---|---|
| 2020/0405498 A1 | 12/2020 | Gray et al. |
| 2020/0405499 A1 | 12/2020 | Gerbec et al. |
| 2020/0405500 A1 | 12/2020 | Cain |

FOREIGN PATENT DOCUMENTS

| | | |
|---|---|---|
| EP | 0 880 950 A1 | 12/1998 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| FR | 3082115 A1 | 12/2019 |
| GB | 2 377 387 A | 1/2003 |
| WO | 92/14423 A1 | 9/1992 |
| WO | 97/00054 A1 | 1/1997 |
| WO | 99/26562 A1 | 6/1999 |
| WO | 99/66867 A1 | 12/1999 |
| WO | 00/12033 A1 | 3/2000 |
| WO | 00/25706 A1 | 5/2000 |
| WO | 00/49977 A1 | 8/2000 |
| WO | 02/19952 A1 | 3/2002 |
| WO | 03/105673 A2 | 12/2003 |
| WO | 2014/133755 A1 | 9/2014 |
| WO | 2017/168208 A1 | 10/2017 |
| WO | 2018049227 A1 | 3/2018 |

OTHER PUBLICATIONS

International Search Report and Written Opinion for Application No. PCT/US2019/019060, dated Jun. 5, 2019.

* cited by examiner

MONOBLOCK EXPANDABLE INTERBODY IMPLANT

CROSS-REFERENCE TO RELATED APPLICATIONS

This application incorporates the entire disclosure of U.S. patent application Ser. No. 17/246,968, titled UNIBODY DUAL EXPANDING INTERBODY IMPLANT, filed May 3, 2021; and U.S. patent application Ser. No. 17/332,284, titled RHOMBOID SHAPED IMPLANTS, filed May 27, 2021 by reference.

FIELD

The present technology is generally related to a unibody expanding interbody implant for use in a medical procedure related to the spine. In some embodiments, disclosed implants may be used in an anterior cervical discectomy and fusion (ACDF) procedure although other uses in other areas of the spine or between two bones are also contemplated.

BACKGROUND

Mechanically operated interbody implants may be used to align and/or realign a patient's spine during a medical procedure. Conventional implants designed for the Thoracic and Lumbar region of the spine often include top and bottom endplates and a mechanical means to separate the top and bottom endplates. The mechanical mechanisms to separate the top and bottom endplates are often cumbersome and require a large footprint that is often unsuitable, for example, for ACDF type surgeries of the cervical portion of the spine.

SUMMARY

The techniques of this disclosure generally relate to a unibody implant that is independently expandable at a first side and a second side opposite the first side.

In one aspect, the present disclosure provides for a unibody implant movable between an expanded position and a contracted position, for example. The unibody implant may extend from a proximal side or end to a distal side or end in a longitudinal direction, extend from a first lateral side to a second lateral side in a lateral direction, and extend from a superior side to an inferior side in a vertical direction, for example. Here, the term longitudinal is used for purposes of defining the direction from the proximal end to the distal end and the term lateral direction is used to define the direction perpendicular to the longitudinal direction. In various embodiments, the unitary expandable body may be defined by an inferior portion, and a superior portion, and the inferior portion may be connected to the superior portion, for example. In various embodiments, a set screw or actuator screw may be rotatably supported by the body and rotatable in a clockwise direction and a counterclockwise direction around a rotation axis. In some embodiments, the rotation axis may extend parallel to the longitudinal direction and in other embodiments the rotation axis may extend in an off angle orientation to the longitudinal direction, for example. For example, the rotation axis may extend in a direction that is angled at about 0 degrees to about 25 degrees with respect to the longitudinal direction, for example. In various embodiments, a plug or wedge may be disposed adjacent to and may be in contact with the set screw, and the plug may further have a first inclined surface facing the distal side, for example. In various embodiments, the set screw may be referred to as an actuating screw and rotation thereof may cause the plug to move, e.g., the set screw may actuate motion of the plug and therefore be referred to as an actuating screw. In various embodiments, the superior portion may comprise a first inclined ramp disposed on an interior surface thereof and facing the first inclined surface of the plug, for example. In various embodiments, the set screw may be movable in the longitudinal direction towards the distal side or end upon rotation of the set screw along the rotation axis, for example. In various embodiments, movement of the set screw in the longitudinal direction towards the distal side urges the first inclined surface of the plug against the first inclined ramp thereby expanding a vertical distance of the body between the superior and inferior sides of the body adjacent the proximal side of the body.

In another aspect, the disclosure provides for a method for expanding and contracting a unibody implant. The method may include the step of providing a unibody implant. In various embodiments, the unibody implant may extend from a proximal side to a distal side in a longitudinal direction, extend from a first lateral side to a second lateral side in a lateral direction, and extend from a superior side to an inferior side in a vertical direction, for example. In various embodiments, the unitary expandable body may be defined by an inferior portion, and a superior portion, and the inferior portion may be connected to the superior portion, for example. In various embodiments, a set screw may be rotatably supported by the body and rotatable in a clockwise direction and a counterclockwise direction around a rotation axis. In some embodiments, the rotation axis may extend parallel to the longitudinal direction and in other embodiments the rotation axis may extend in an off angle orientation to the longitudinal direction, for example. In various embodiments, a plug may be disposed adjacent to and in contact with the set screw, and the plug may have a first inclined surface facing the distal side, for example. In various embodiments, the superior portion may comprise a first inclined ramp disposed on an interior surface thereof and facing the first inclined surface of the plug, for example. In various embodiments, the set screw may be movable in the longitudinal direction towards the distal side upon rotation of the set screw along the rotation axis, for example. In various embodiments, movement of the set screw in the longitudinal direction towards the distal side urges the first inclined surface of the plug against the first inclined ramp thereby expanding a vertical distance of the body between the superior and inferior sides of the body adjacent the proximal side of the body. The method may include the step of rotating the set screw such that it linearly translates from the proximal side towards the distal side and the step of pushing the plug, by the set screw, towards the distal side, for example. The method may further include the step of urging, by the plug, the first inclined ramp of the superior portion up and away from the inferior portion, for example.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 13 is a reference drawing showing the human spine of which various disclosed implant embodiments may be installed in.

DETAILED DESCRIPTION

Figure 1:
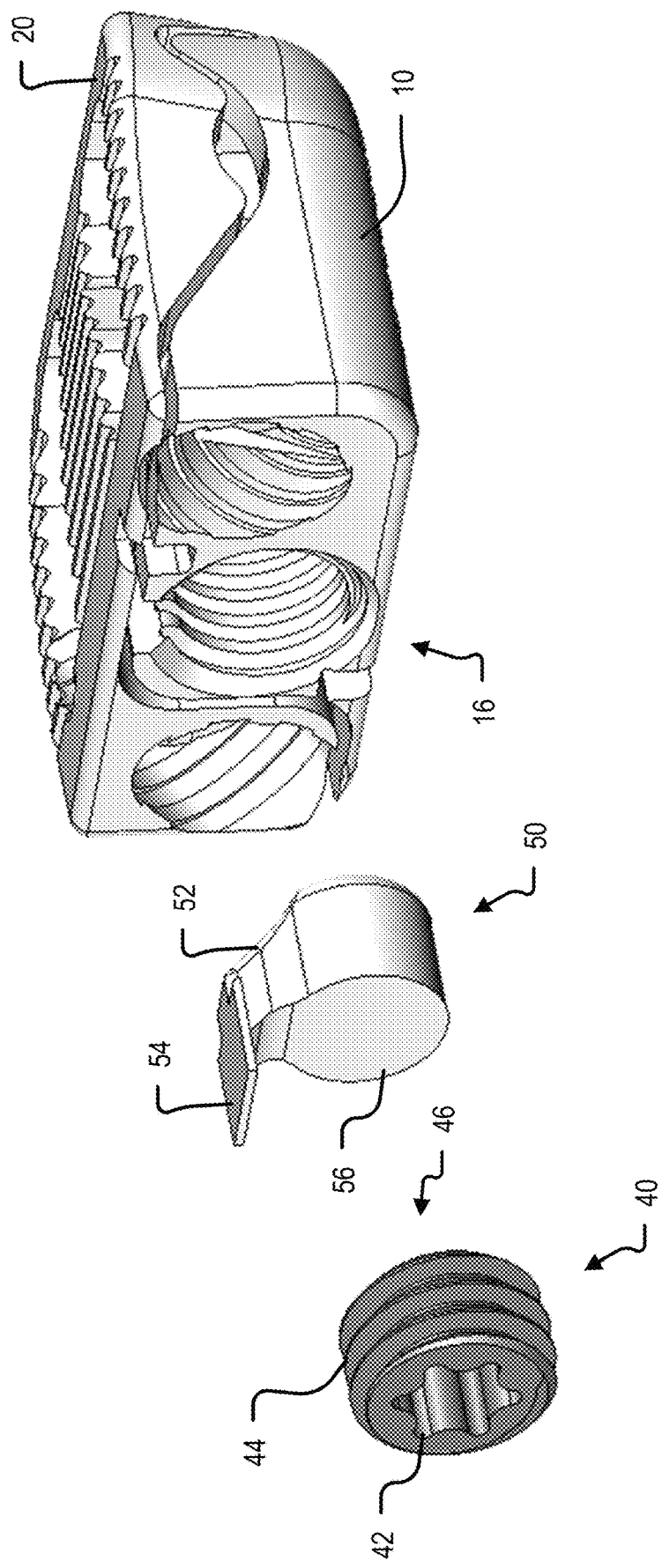
FIG. 1 is a front exploded parts view of an implant.
Figure 2:
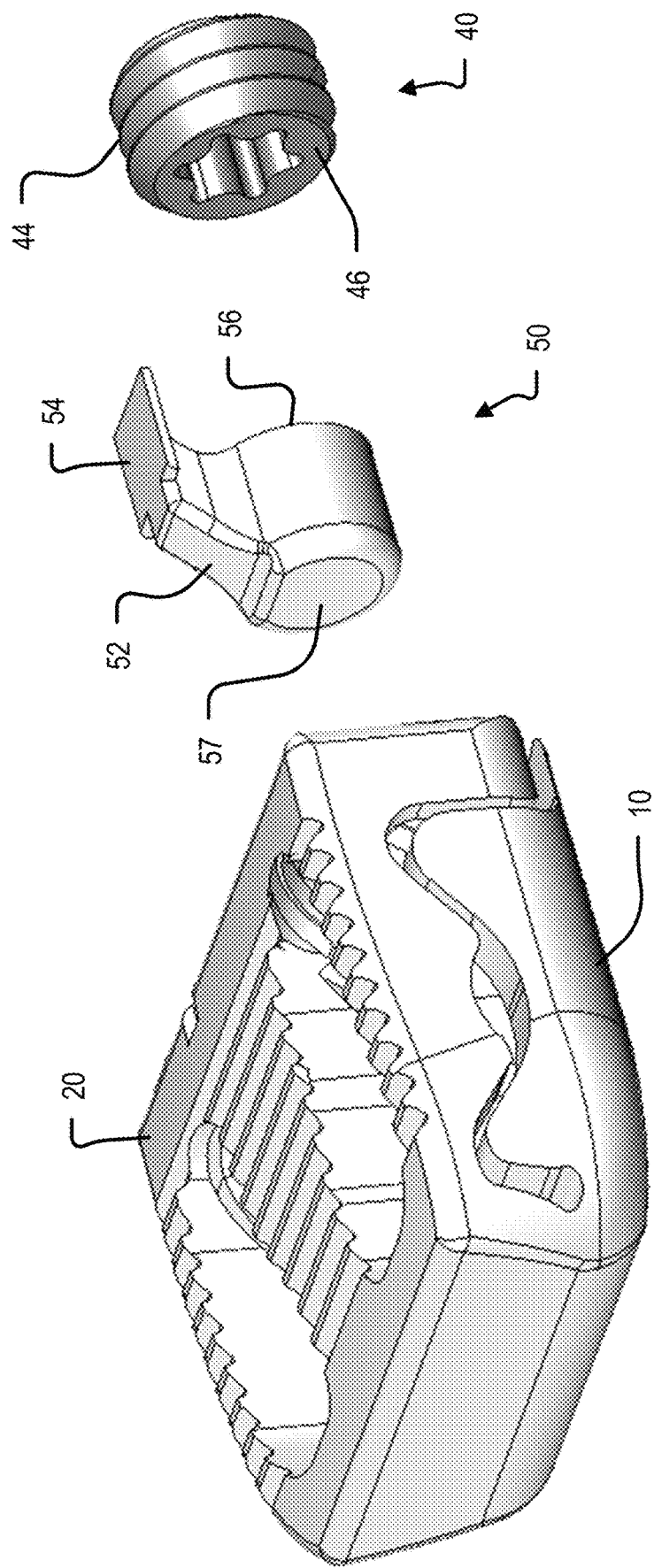
FIG. 2 is a rear exploded parts view of an implant.

Embodiments of the present disclosure relate generally, for example, to spinal stabilization systems, and more particularly, to a unibody implant having a superior portion and an inferior portion that are connected and expandable and contactable by action of a set screw and a plug. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring to FIGS. 1-12 generally, various spinal implant 100 embodiments are disclosed. The components of spinal implant 100 can be fabricated from biologically acceptable materials suitable for medical applications, including metals, synthetic polymers, ceramics and bone material and/or their composites. For example, the components of spinal implant 100, individually or collectively, can be fabricated from materials such as stainless steel alloys, commercially pure titanium, titanium alloys, Grade 5 titanium, superelastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Referring generally to FIGS. 1-12 an implant 100 is disclosed. The implant 100 may be used for an ACDF surgery in the cervical area of the spine (see FIG. 13), and expand in various planes of a patient 1 (see FIG. 14). However, other uses within the lumbar and/or thoracic area of the spine or between two bones or bone portions or within the void located in a bone are also contemplated. The present disclosure aims to reduce the complexity of mechanical mechanisms to cause distraction, lordosis, and/or kyphosis while increasing the available interior space of an implant by minimizing the size of the moving mechanism that causes distraction, lordosis, and/or kyphosis. At least one advantage of minimizing the size of the moving mechanism is that a relatively greater volume of a bone growth promoting material may be placed and/or injected inside of the implant for promoting fusion between adjacent vertebrae of a patient.

Implant 100 may be referred to as a monoblock implant, monolithic implant unibody implant, and/or unitary implant in some embodiments. As used herein, the terms monolithic, unitary, and/or unibody shall have their ordinary technical meaning. For example, referring to a component that a person of ordinary skill in the art would consider being formed as a continuous single piece. However, it shall be understood that in various embodiments a continuous single piece may have respective portions that are connected to one another to form the continuous single piece.

Implant 100 may include an inferior portion 10 and a superior portion 20 that define the outside surfaces of implant 100. It shall be understood that although implant 100 is described herein as being composed of an inferior portion 10 and a superior portion 20 that these portions are securely connected to one another to form an implant 100. For example, the inferior portion 10 is connected to the superior portion 20. In various embodiments, the implant 100 is expandable between a contracted position and an expanded position by movement of a set screw 40 which acts against and pushes a plug 50. In various embodiments, plug 50 may also be referred to as a barrel and/or include a hollow center. In various embodiments, set screw 40 may be positioned anteriorly of plug 50 and rotation of set screw 40 may cause set screw 40 to advance and therefore push plug 50.

In various embodiments, the set screw 40 may include a drive feature 42 (may also be referred to as a drive end aperture) including a plurality of peaks and valleys disposed on an interior circumferential surface, and a thread pattern 44 disposed on an exterior circumferential surface. Drive feature 42 may extend through set screw 40 and, in the illustrated embodiment, drive feature 42 may resemble a hexalobular shaped aperture. However, other designs are contemplated, e.g., the drive feature 42 may resemble the geometry of the tip of a torx driver, hex driver, phillips driver, square head driver, polygonal driver, or any combination thereof. In various embodiments, a rear surface 46 of set screw 40 may be configured to directly contact and push against a front surface 56 of plug 50. Various surgical tools may rotate set screw 40, for example the surgical tool 200 disclosed in U.S. application Ser. No. 17/246,968, the entire contents of which are incorporated herein by reference. In the example embodiment, rear surface 46 may have a relatively flat and/or substantially planar smooth surface surrounding the open aperture shape of drive feature 42.

In the example embodiment, plug 50 includes a base portion having a substantially cylindrical shape that transitions into an upper portion including a first inclined surface 52 and a stabilizing element 54. In the example embodiment, first inclined surface 52 may extend between second inclined surface 53 and stabilizing feature 54, for example. In various embodiments, stabilizing feature 54 may be disposed on a superior portion of plug 50 and extend towards a proximal side of implant 100 and/or an anterior side of implant 100 depending on orientation. Stabilizing feature 54 may provide a bearing surface for providing a stabilizing function between the inferior portion 10 and superior portion 20, for example, which will be explained in further detail below. Additionally, first inclined surface 52 may act against a corresponding inclined surface of implant 100 to cause expansion of implant 100, for example, which will be explained in further detail below. Similarly, second inclined surface 53 may act against a corresponding inclined surface of implant 100, and/or act as a bearing surface for a corresponding portion of implant 100 when implant 100 is in an expanded configuration, for example, which will be explained in further detail below.

In various embodiments, the set screw 40 may be rotatably engaged with a first threaded aperture 16 of the inferior portion 10 and the cylindrical base portion of plug 50 may be coaxially aligned with set screw 40. For example, the cylindrical base portion may have a central point positioned approximately in a center of a circle defining, at least partly, front surface 56 and the central point may be coaxially aligned with a central axis of rotation of set screw 40. However, it shall be understood that in other embodiments, such coaxial symmetry is not required as set screw 40 may contact and push against surface 56 of plug 50 and therefore move plug 50 without being coaxially aligned. Additionally, in various embodiments plug 50 may optionally be hollow and/or include an aperture coaxially aligned with the aperture of drive feature 42, for example the cross section drawing of FIG. 11. In various embodiments, the threaded aperture 16 may include a discontinuity at an upper end thereof for accommodating a corresponding portion of superior portion 20 and/or plug 50. For example, a discontinuity in the uppermost surface of inferior portion 10 that may accommodate stabilizing feature 54. As will be explained in further detail below, an interior of the superior portion 20 may include a first inclined ramp 26 (see FIG. 8) of which the first inclined surface 52 of plug 50 may act against. For example, when rotating the set screw 40 it may move forward and backward in a longitudinal direction within the first threaded aperture 16 thereby pushing plug 50 and urging the first inclined surface 52 of plug 50 against the first inclined ramp 26 to expand a vertical height of the implant 100.

Figure 3:
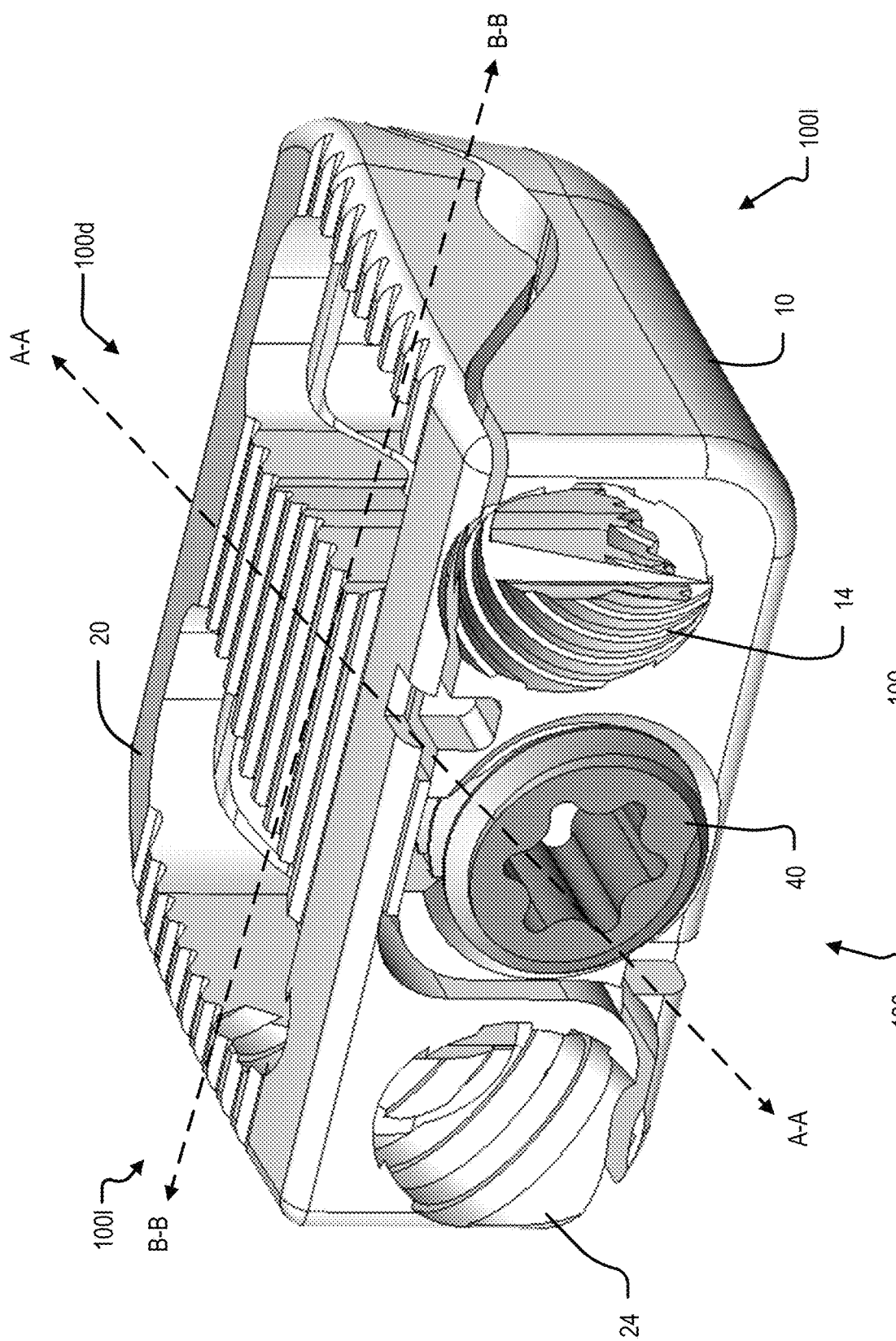
FIG. 3 is a front perspective view of an implant.
Figure 4:
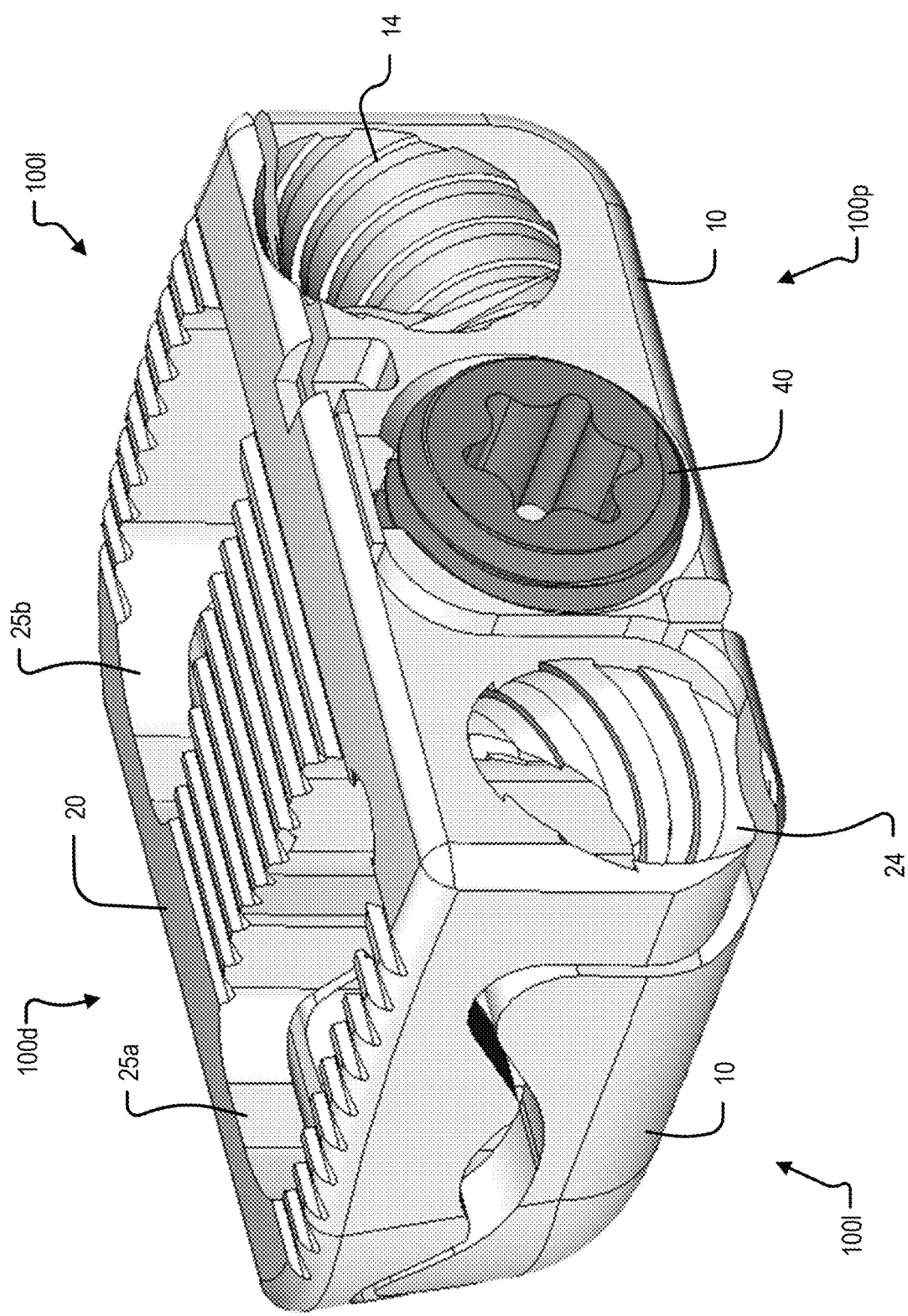
FIG. 4 is an alternate front perspective view of an implant.
Figure 5:
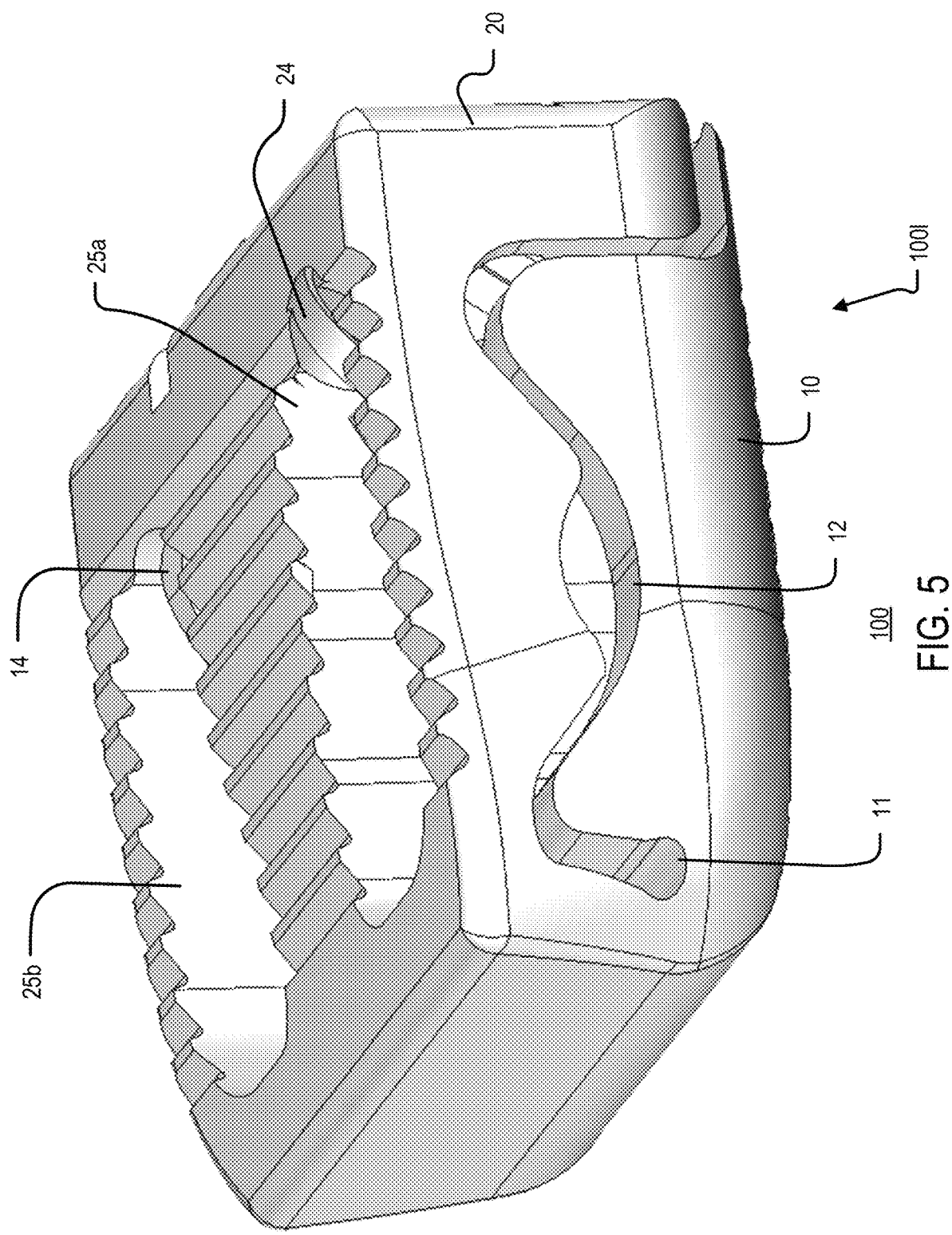
FIG. 5 is a side perspective view of an implant.
Figure 6:
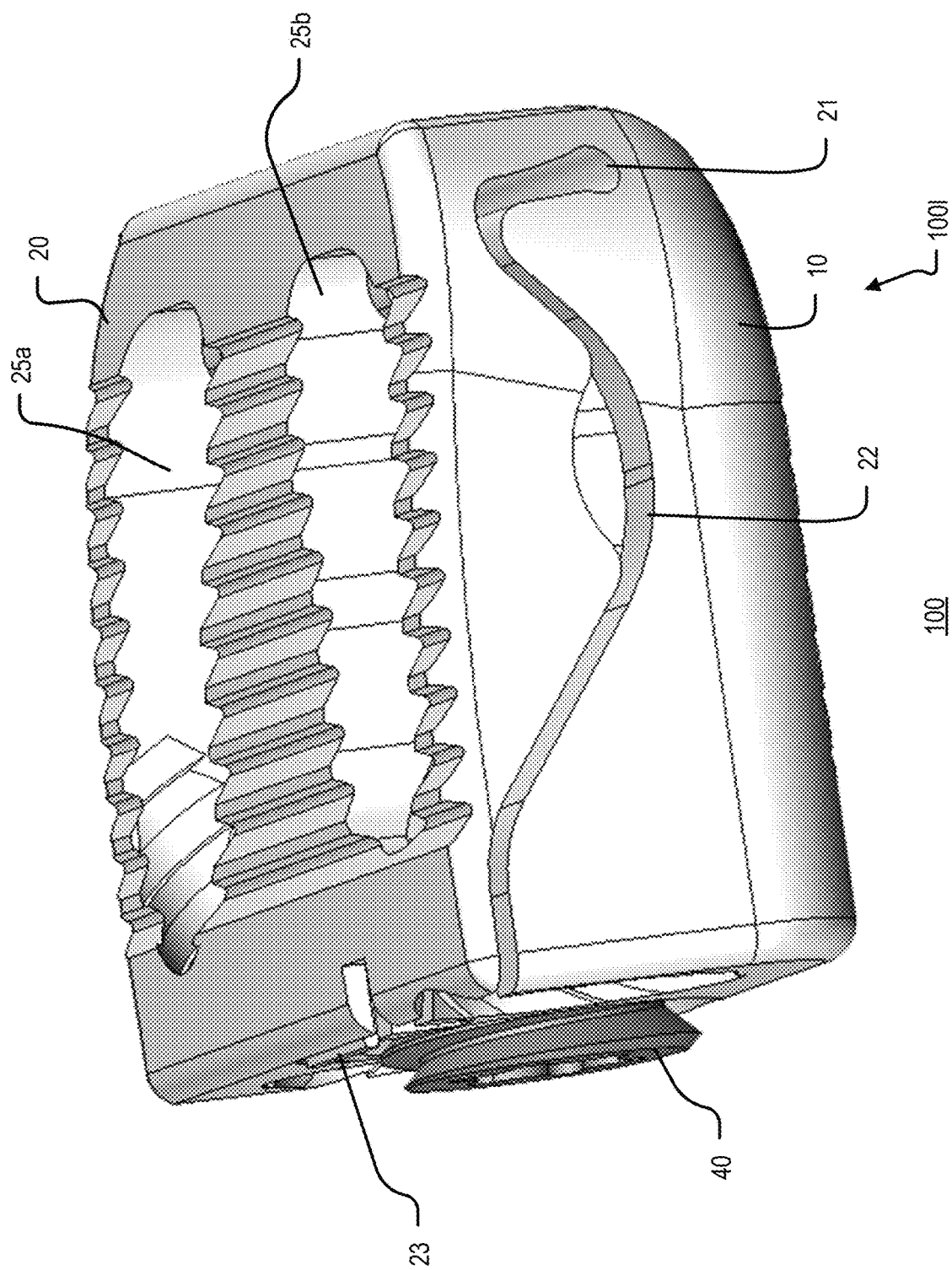
FIG. 6 is an alternate side perspective view of an implant.
Figure 7:
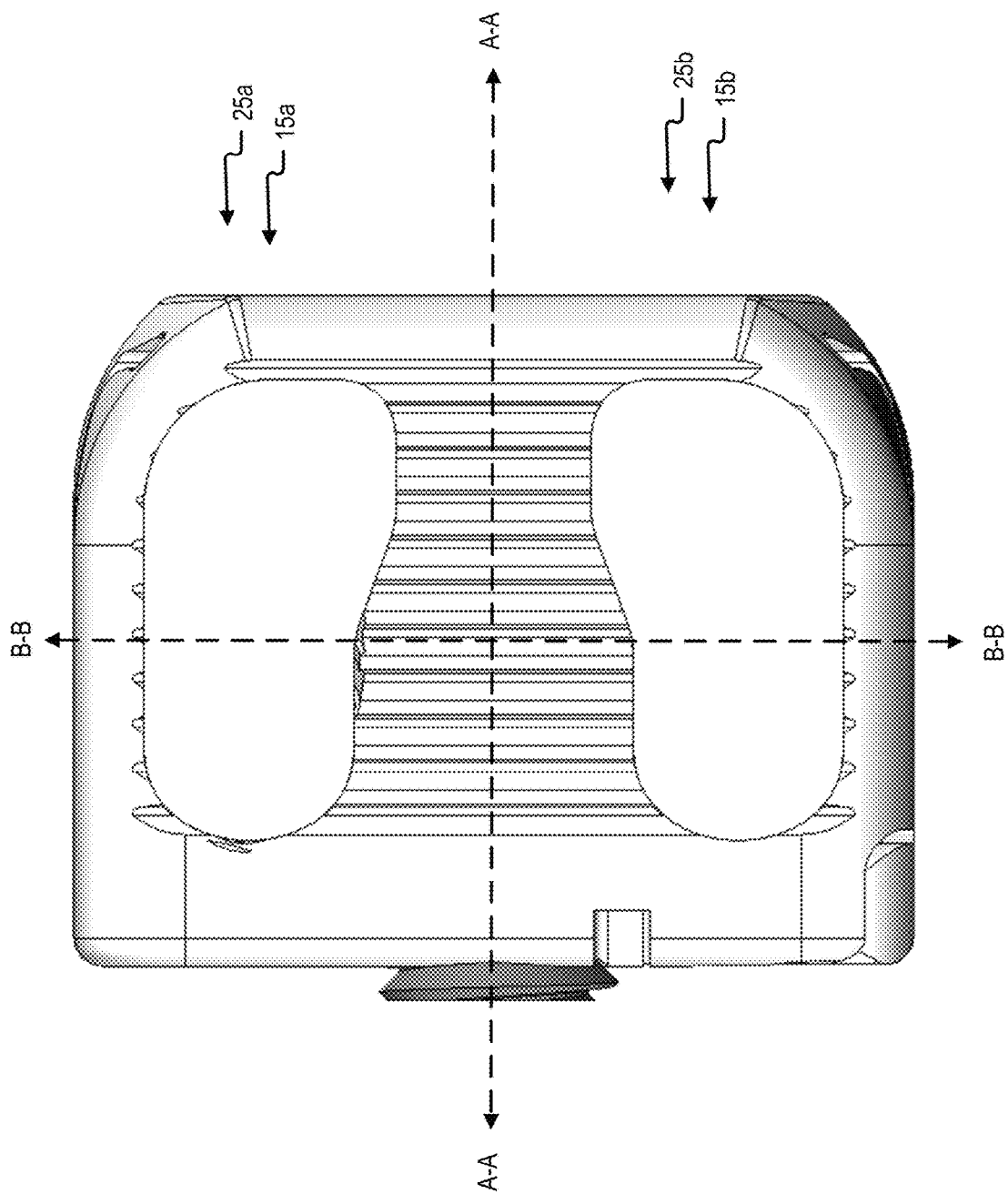
FIG. 7 is a top down view of an implant.

FIGS. 3 and 4 are various perspective views of an implant 100, FIGS. 5 and 6 are various perspective views of an implant 100, and FIG. 7 is a top down view of implant 100. In the example embodiment, implant 100 may extend in a longitudinal direction along axis A-A from a proximal side 100p to a distal side 100d. Those with skill in the art will appreciate that proximal side 100p may be referred to as an anterior side and distal side 100d may be referred to as a posterior side (and vice versa) depending on the orientation of implant 100. Implant 100 may extend in a lateral direction along axis B-B from a first lateral side 100l to a second lateral side 100l, for example. Additionally, implant 100 may include a superior side 100s (top surface) and an inferior side 100I (bottom surface). In various embodiments, the superior side 100s may be defined by the superior portion 20 and the inferior side 100I may be defined by the inferior portion. Additionally, in various embodiments, a proximal end of implant 100, for example a front vertical face of implant 100 may be defined by a proximal surface of inferior portion 10 and a proximal surface of superior portion 20. For example, the front face of implant 100 may be defined by both the superior portion 20 and inferior portion 10 as shown in FIG. 3. It shall also be appreciated that a vertical spacing between the superior portion 20 and inferior portion 10 is expandable and contactable at the proximal side 100p of implant 100 because the superior portion 20 and inferior portion 10 may not be rigidly connected at the proximal side 100p. Additionally, in various embodiments a distal end of implant 100, for example a rear surface of implant 100, may be defined by a distal surface of inferior portion 10 and a distal surface of superior portion 20. For example, the rear face of implant 100 may be defined by a region where both the superior portion 20 and inferior portion 10 are connected as shown in FIG. 5. It shall also be appreciated that in various embodiments a vertical spacing between the superior portion 20 and the inferior portion 10, at the distal side 100d of implant 100, may not be adjustable and/or expandable because the superior portion 20 and inferior portion 10 are connected at the distal side 100d. For example still, the distal side 100d of implant 100 may act as a hinge and/or function as a hinge that undergoes an elastic deformation in an expanded configuration.

Referring to FIGS. 3-7, implant 100 may include a plurality of slotted apertures 15a, 15b, 25a, and 25b to facilitate fusion of adjacent vertebrae, for example. In various embodiments, slotted apertures 15a, 15b, 25a, and 25b may be vertically aligned (see top down view of FIG. 7). Additionally, slotted apertures 15a, 15b, 25a, 25b may be packed with a bone growth promoting material to facilitate a fusion process. In various embodiments, implant 100 may include at least one bone screw aperture 14, 24. For example, the proximal side 100p of implant 100 may include a first bone screw aperture 14 that extends through a vertical face of inferior portion 10 on the proximal side 100p through a slotted aperture 15b of the inferior side 100I. In various embodiments, a portion of first bone screw aperture 14 may be formed in the inferior portion 10 and/or have at least a portion thereof formed in the inferior surface 100I. Additionally, the proximal side of implant 100 may include a second bone screw aperture 24 that extends through a vertical face of superior portion 20 on the proximal side 100p through a slotted aperture 25a of the superior side 100s. In various embodiments, a portion of second bone screw aperture 24 may be formed in the superior portion 20 and/or have at a least a portion thereof formed in the superior surface 100s. In various embodiments, bone screw apertures 14, 24 may be conically shaped and include various lip portions for retaining a head portion of a bone screw (not illustrated). In other embodiments, bone screw apertures 14, 24 may comprise an aperture maintaining substantially the same internal diameter, i.e., not tapering and/or conical. Additionally, in various embodiments bone screw apertures 14, 24 may allow for some freedom of movement when installing a bonescrew therein by accommodating about +/−5 degrees in any direction relative to a target alignment, for example.

Implant 100 may include at least one slit 12, 22 on each lateral side 1001. For example, a first slit 12 may take the form of a discontinuity extending in the longitudinal direction along the first lateral surface 1001 between the inferior portion 10 and the superior portion 20, for example. The first slit 12 may follow an undulating curved path and include a generally teardrop-shaped cutout 11 proximate the distal side 100d to facilitate the expansion of implant 100, for example. In various embodiments, and as illustrated, the undulating curved path of first slit 12 may be configured to facilitate an elastic deformation of implant 100 by allowing enough of a void space for the superior portion 20 to expand away from and relative to the inferior portion 10, for example. Similarly, a second slit 22 may take the form of a discontinuity extending in the longitudinal direction along the second lateral surface 1001 between the inferior portion 10 and the superior portion 20, for example. The second slit 22 may include a generally teardrop-shaped cutout 21 proximate the distal side 100d. In various embodiments, and as illustrated, the undulating curved path of first slit 12 may be configured to facilitate an elastic deformation of implant 100 by allowing enough of a void space for the superior portion 20 to expand away from and relative to the inferior portion 10, for example.

In the example embodiment, first slit 12 may extend along an undulating path along lateral side 1001 from tear drop cutout 11 towards a proximal side of implant 100 and adjoin the proximal end of implant 100 adjacent the inferior side 1001. For example, first slit 12 may extend from tear drop cutout 11 to the front face of implant 100 and transition into proximal slit 23. Similarly, in the example embodiment second slit 22 may extend along an undulating path along lateral side 1001 from tear drop cutout 21 to the front face of implant 100 and adjoin the proximal end of implant 100 adjacent the superior side 100s. For example, second slit 22 may extend from tear drop cutout 21 to the front face of implant 100 and transition into proximal slit 23. Proximal slit 23 may extend laterally along the proximal face of implant 100 between the first lateral end 1001 and second lateral end 1001. In the example embodiment, proximal slit 23 adjoins first slit 12 adjacent the inferior side 1001 of implant 100 and adjoins second slit 22 adjacent the superior side 100s. In this way, implant 100 may be disconnected and/or substantially disconnected on the first lateral side 1001, second lateral side 1001, and proximal side 100p yet remain connected at the distal side 100d.

Figure 8:
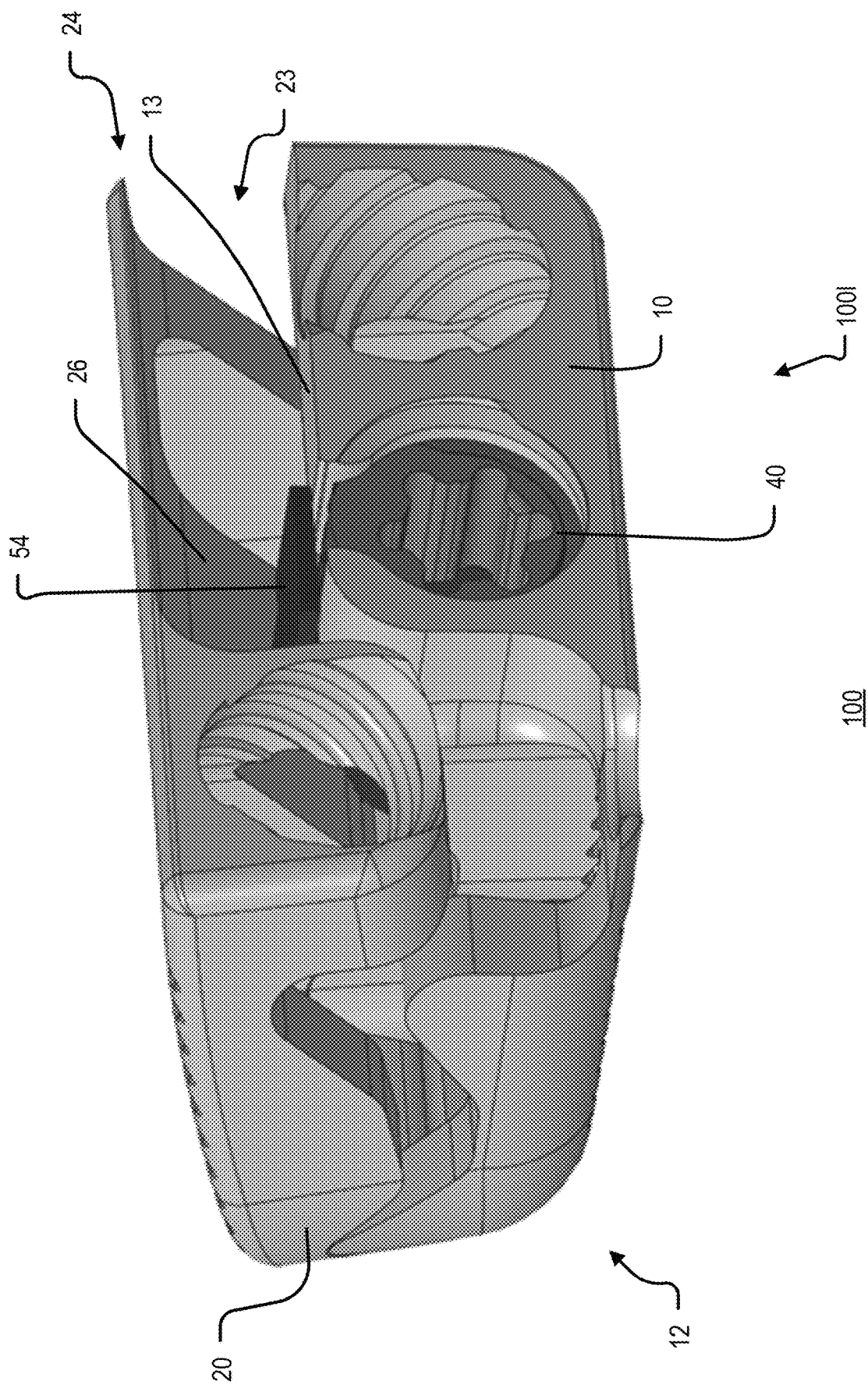
FIG. 8 is a side view of an implant in an expanded configuration.
Figure 9:
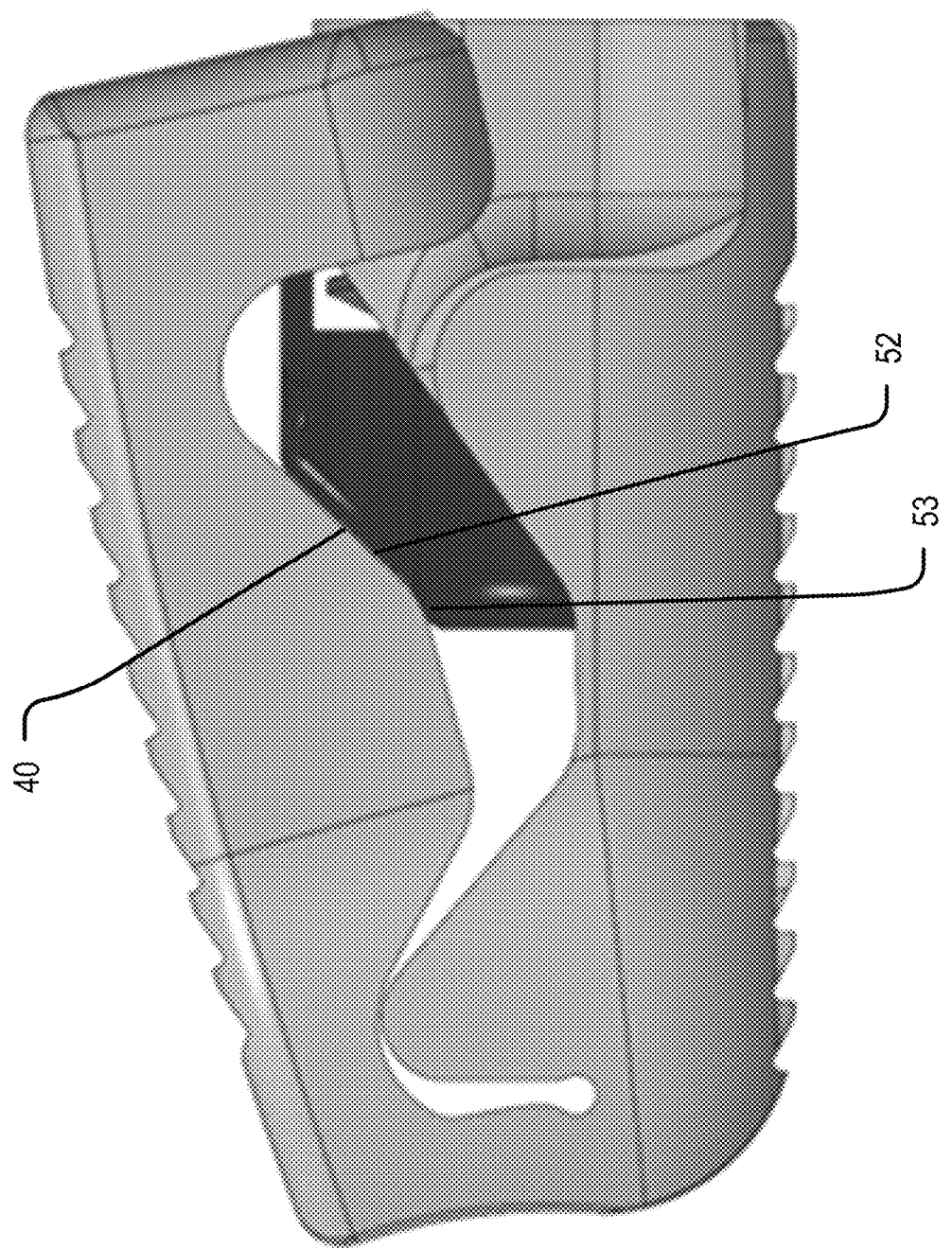
FIG. 9 is a side view of an implant in an expanded configuration.

With reference to FIGS. 8 and 9, in various embodiments slits 12, 22 and teardrop-shaped cutouts 11, 21 may be featured on both lateral sides 1001 of implant 100. The slits 12, 22 and teardrop-shaped cutouts 11, 21 may be configured to facilitate the expansion and contraction of implant 100 while the inferior portion 10 and superior portion 20 remain connected together at the distal side. For example, in an expanded configuration the slits 12, 22 and teardrop-shaped cutouts 11, 21 facilitate the pivoting of the superior portion 20 relative to the inferior portion 10 while slit 23 is enlarged (relative to a contracted configuration), for example. For example, by rotating set screw 40 such that it linearly translates from a proximal side 100p towards the distal side 100d and pushes plug 50 from the proximal side 100p towards the distal side 100d. In moving plug 50 towards the distal side 100d of implant 100 the first inclined surface 52 acts against the interior ramped surface 26 and pushes the superior portion 20 up and away from the inferior portion 10 while the distal side 100d of implant 100 is elastically deformed to allow the expansion. As seen best in the side profile of FIG. 9, first inclined surface 52 may act against inclined ramp 26 and second inclined surface 53 may act against and/or support a lower most surface of inclined ramp 26. In various embodiments, first inclined surface 52 may be inclined by a greater degree than second inclined surface 53 and each may be inclined by a degree corresponding to the inclination of inclined ramp 26, for example.

Consistent with the above disclosure, actuation of set screw 40 and linear translation of plug 50 may cause a lordotic angle of implant 100 to be adjusted and slits 12, 22, 23, and tear drop cutouts 11, 21 may facilitate the elastic deformation of implant 100 at the distal side 100d. As seen best in FIG. 8, stabilizing feature 54 of plug 50 may prevent plug 50 from rotating while also providing a bearing surface. For example, in various embodiments a bottom planar surface of support feature 54 may contact and/or slide across planar upper surface 13 of inferior portion 10. In some embodiments, not illustrated, planar upper surface 13 of inferior portion 10 may include a groove and/or recess for nesting and/or mating with support feature 54.

Figure 10:
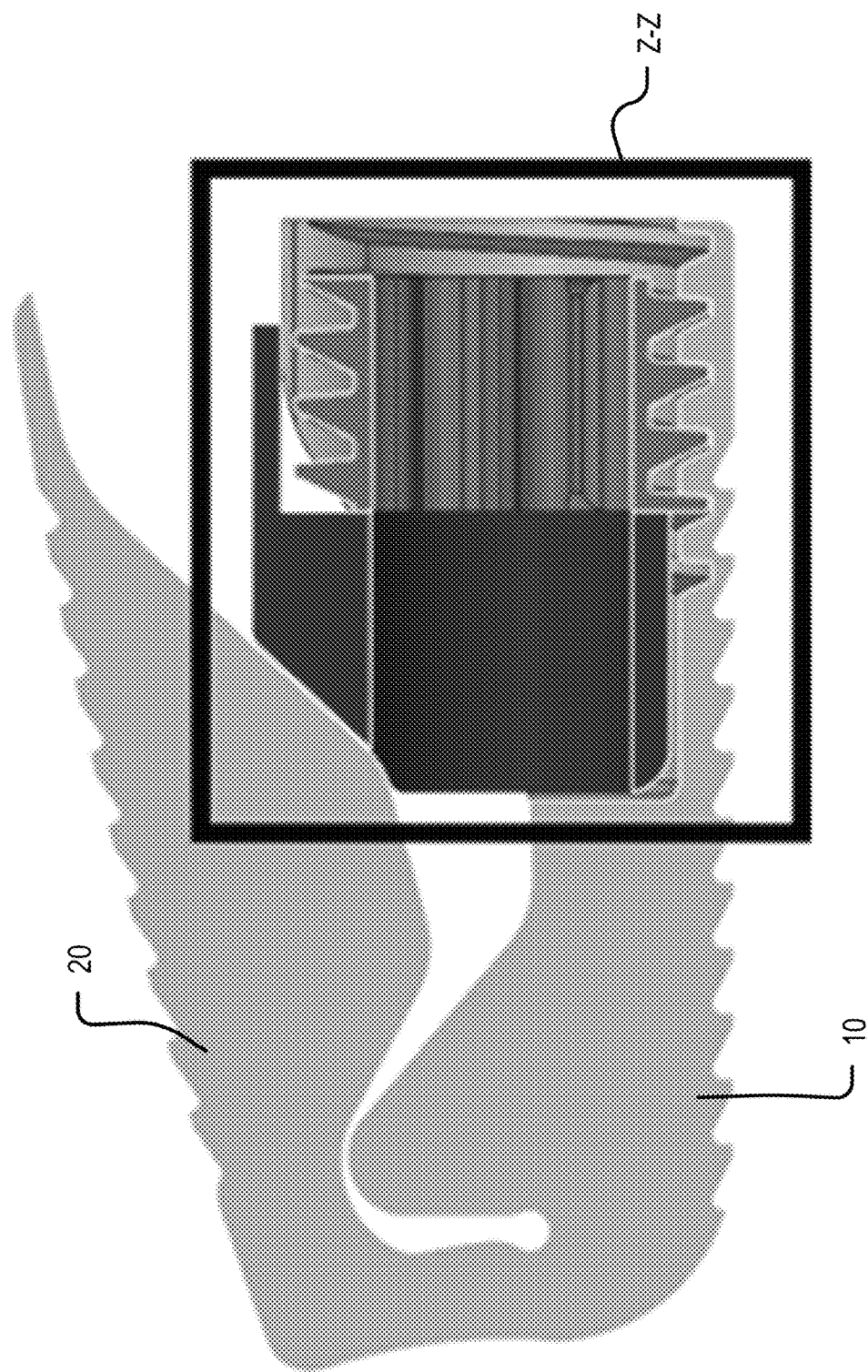
FIG. 10 is a cross section view of an implant in an expanded configuration.
Figure 11:
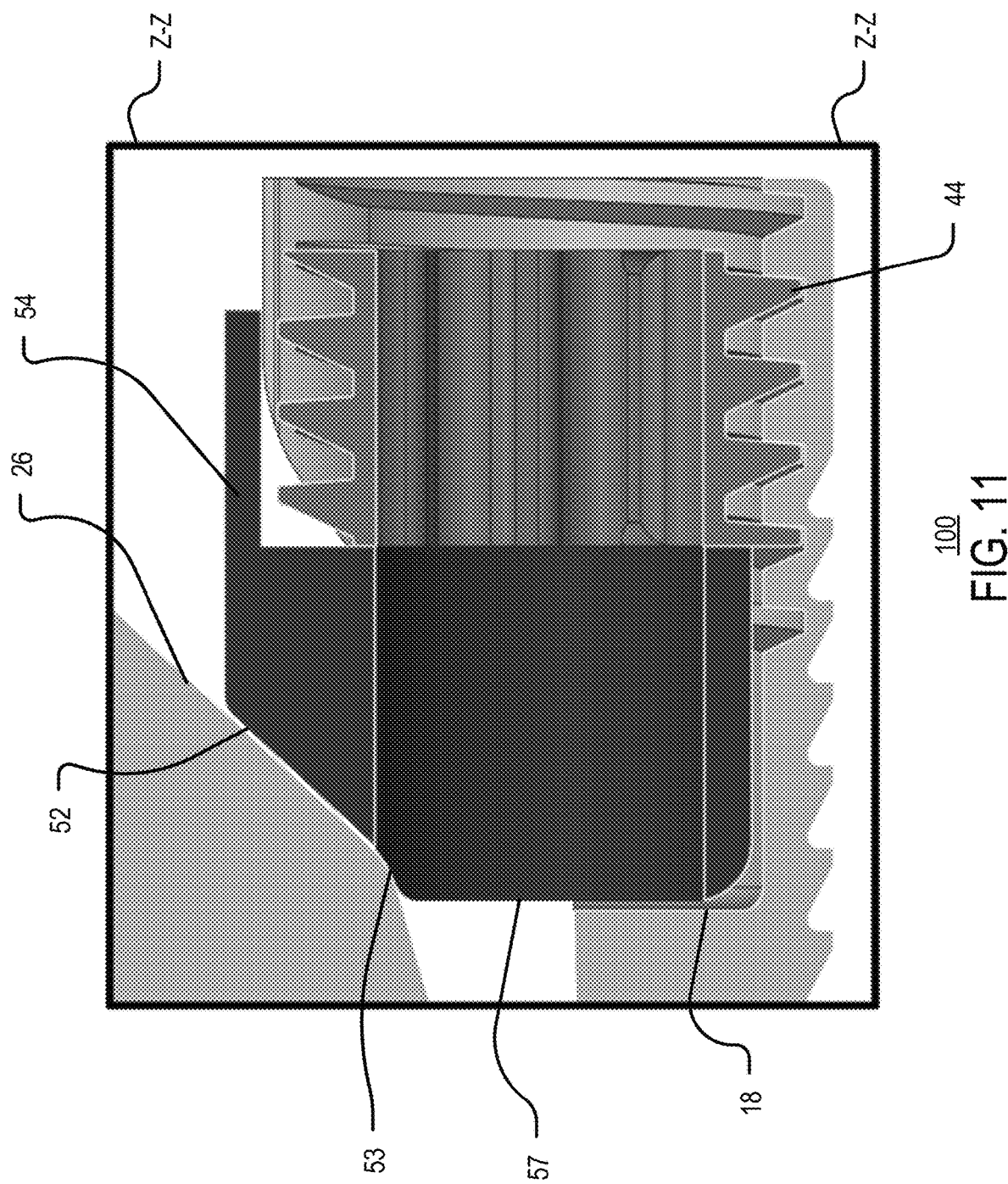
FIG. 11 is an enlarged view of section Z-Z of FIG. 10.

FIG. 10 illustrates a first cross section illustration through the center of implant 100 in the longitudinal direction and/or through longitudinal axis A-A. FIG. 11 illustrates an enlarged view of region Z-Z of FIG. 10. In the example illustration, it is shown that set screw 40 has pushed plug 50 all the way to a maximum expanded configuration. For example, rotating set screw 40 may cause threads of thread pattern 44 to rotate within threaded aperture 16 such that set screw 40 advances and pushes plug 50. In the maximum expanded configuration, a rear surface 57 of plug 50 has abutted against a stop feature 18 of inferior portion 10. Stop feature 18 may be a surface or wall extending in a vertical direction, for example. Stop feature 18 may prevent the accidental over expansion of implant 100 such that the only type of deformation that can occur is an elastic deformation, i.e., stop feature 18 may prevent the accidental occurrence of a plastic deformation be preventing plug 50 from advancing too far. Additionally, it is shown that support feature 54 provides a bearing surface whereby forces from superior portion 20 may be transferred to inferior portion 10 where an underside of support feature 54 contacts upper surface 13 of inferior portion 10, for example. Additionally, ramped surface 26 may directly contact and bear down against first inclined surface 52 and/or second inclined surface 53, for example. In this way, compressive forces from adjacent vertebrae of a patient may be transferred between the inferior portion 10 and superior portion 20.

Figure 12:
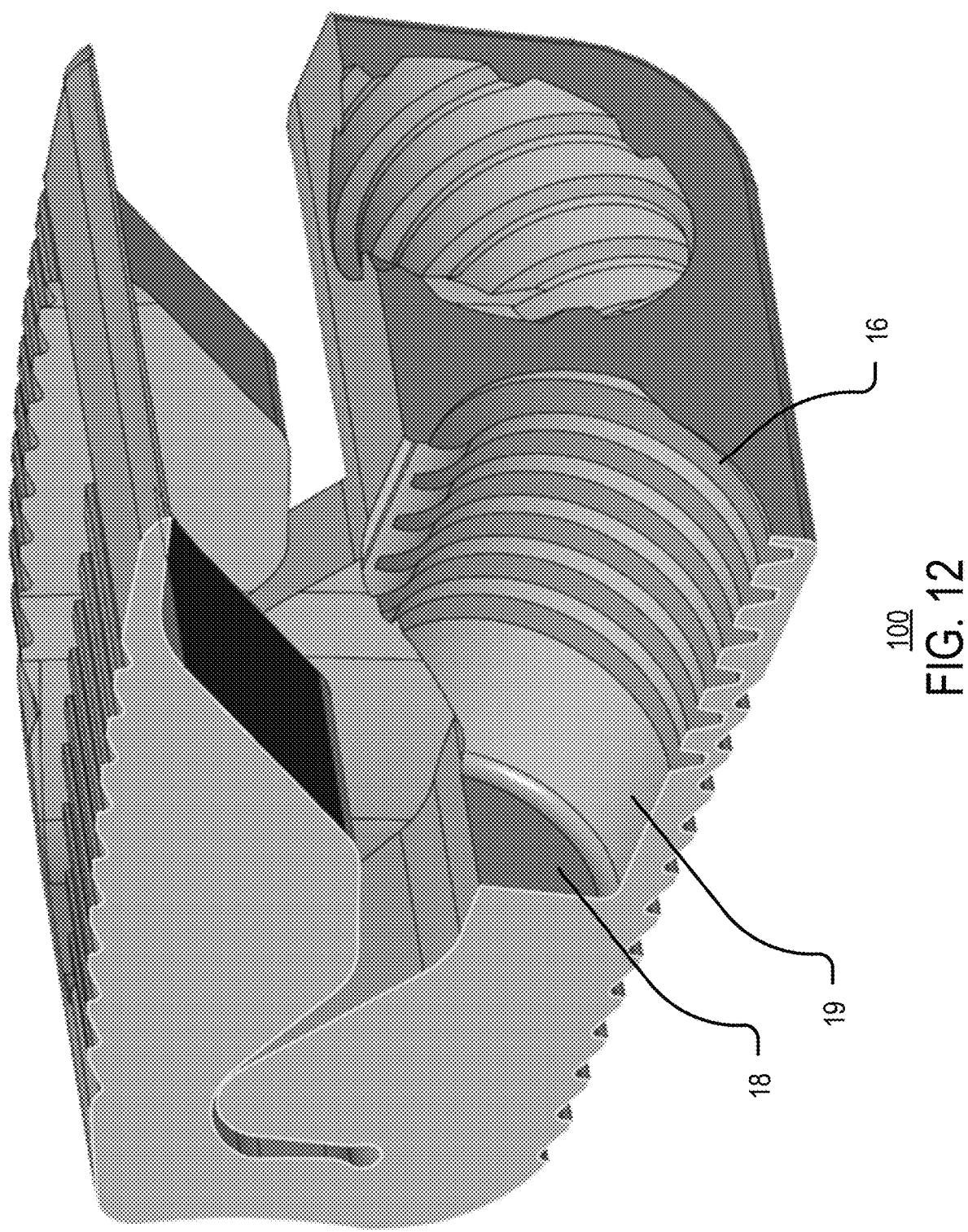
FIG. 12 is a perspective cross section view of an implant in an expanded configuration with some components removed for ease of understanding.

FIG. 12 is a perspective cross section drawing with set screw 40 and plug 50 removed for ease of understanding of the internal geometry of implant 100. In the example embodiment, threaded aperture 16 may include a thread pattern that extends a portion of the distance between the proximal face of implant 100 and stop feature 18. For example, the thread pattern of threaded aperture 16 may terminate where the threads adjoin plug cavity 19. Plug cavity 19 may be a smooth arcuate surface corresponding to the outside diameter of the lower cylindrical portion of plug 50, for example. Plug cavity 19 may be closed, at least partially, at a distal side thereof by stop feature 18, as explained above. In various embodiments, and as illustrated in FIG. 12, the geometry of plug cavity 19 may correspond to an arc of a circle having a radius that approximates the minimum diameter portion of the threads of threaded aperture 16. For example, in a lateral cross section, plug cavity 19 may be considered a portion of a circle having a diameter that corresponds to the minimum diameter of the thread pattern of threaded aperture 16, for example. This arrangement may facilitate plug 50 being able to pass through threaded aperture 16 during assembly, for example.

Consistent with the disclosure herein, various embodiments of implant 100 may include three distinct and unitary components, an implant body formed of a superior portion 20 and inferior portion 10, a set screw 40, and a plug 50. Additionally, in various embodiments, implant 100 may be pre-assembled. For example, the plug 50 may be insert through threaded aperture 16 and into plug cavity 19 and set screw 40 may be threadably engaged with threads of threaded aperture 16 keeping plug 50 within the interior of implant 100. In some embodiments, not illustrated, a locking feature may be added to prevent the set screw 40 from backing out. For example, a locking feature may include a pivoting arm disposed on the proximal face of implant 100 that may rotate between a locked and unlocked position. In the locked position, the pivoting arm may block set screw 40 from backing out and in the unlocked position the pivoting arm may be pivoted away from threaded aperture 16 such that set screw 40 may be removed. In other embodiments, a second set screw (not illustrated) may be installed behind the first set screw 40 to cause jamming.

Figure 13:
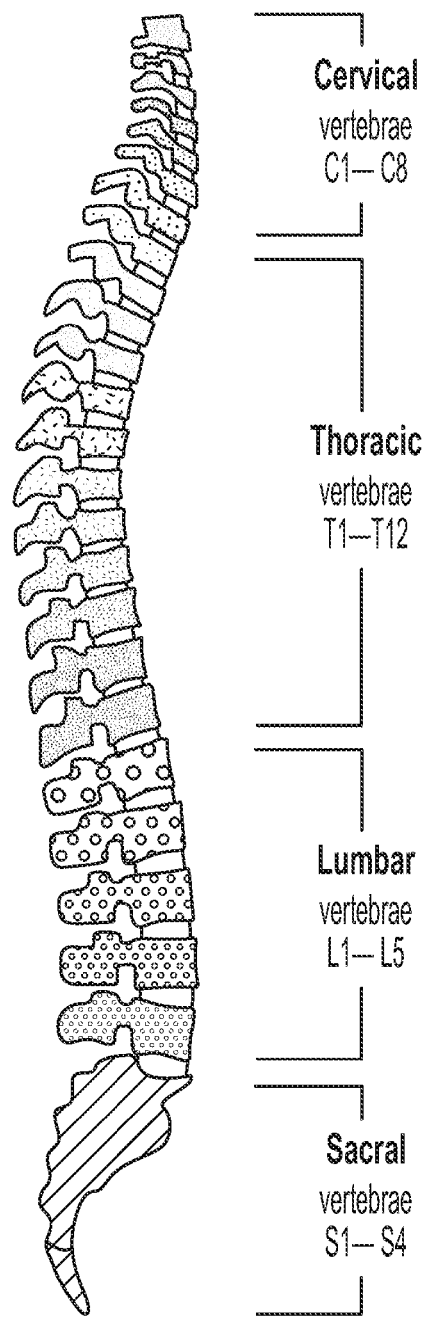
Figure 14:
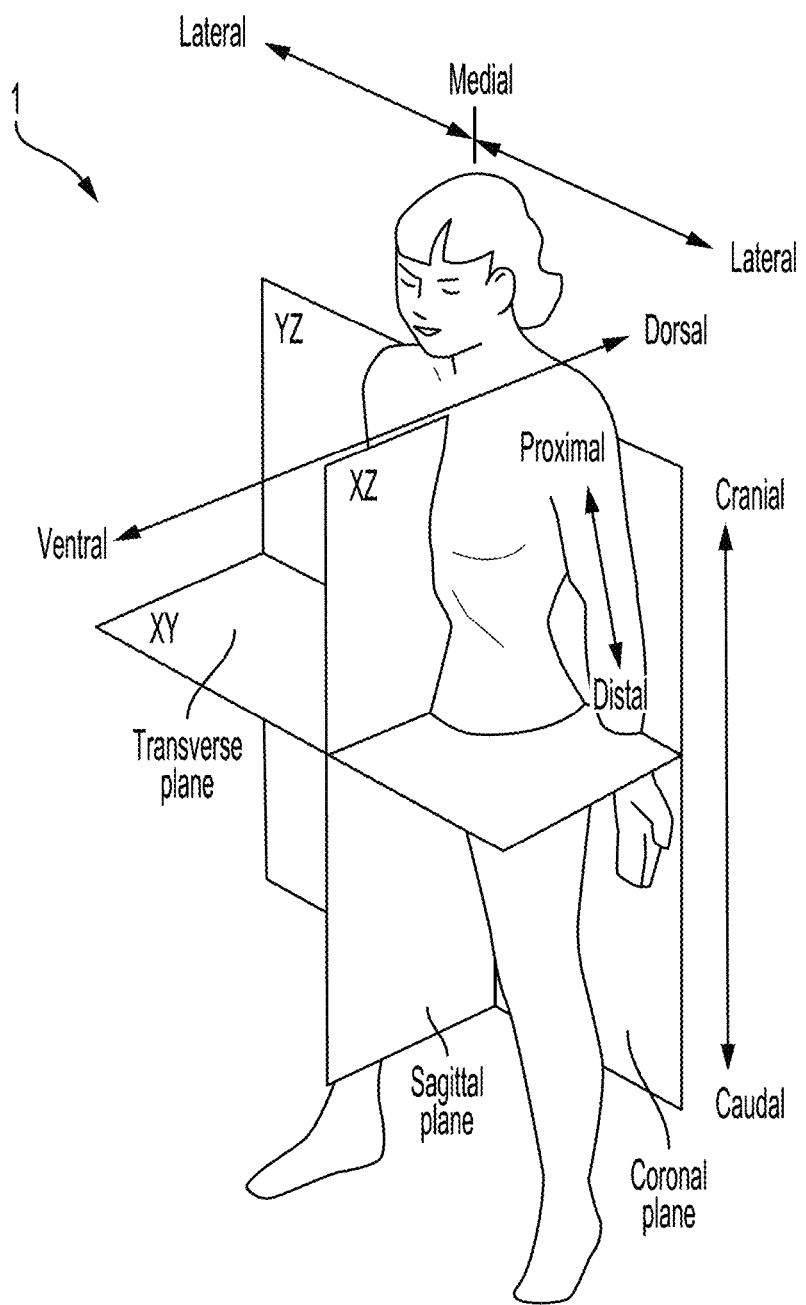
FIG. 14 is a reference drawing showing various planes and reference directions of which the various disclosed implant embodiments may move in or act in with respect to a patient.

FIG. 13 is a reference drawing showing the human spine of which various disclosed implant embodiments may be installed in. FIG. 14 is a reference drawing showing various planes and reference directions of which the various disclosed implant embodiments may move in or act in. In operation, an end user such as a surgeon may place implant 100 between two adjacent vertebrae. Thereafter, the surgeon may lordotically expand implant 100 by rotating set screw 40 thereby pushing plug 50 distally and pushing superior portion 20 away from inferior portion 10. The surgeon may stop the set screw 40 at any appropriate position and the implant 100 may be continuously adjustable between a non-expanded position and the maximum expanded position. In some embodiments, implant 100 may have about 2 degrees to about 6 degrees of lordosis in a fully collapsed position and in other embodiments implant 100 may have about 4 degrees of lordosis in the fully collapsed position. Similarly, in some embodiments implant 100 may have about 12 degrees to about 18 degrees of lordosis in a fully expanded position and in other embodiments implant 100 may have about 15 degrees or lordosis in the fully expanded position.

In various embodiments, it is contemplated that the implant 100 may be filled with a bone growth promoting material that is either solid or fluid and flowable. In at least one embodiment, a flowable bone growth promoting material may be injected through the hollow set screw 40 and through a hollow embodiment of plug 50 such that the flowable graft material enters into the interior of implant 100. For example, as described in detail in U.S. patent application Ser. No. 17/246,968, the entire contents of which are incorporated herein by reference.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. A unibody intervertebral implant movable between a contracted position and an expanded position, comprising:
   a unitary expandable body extending from a proximal side to a distal side in a longitudinal direction, extending from a first lateral side to a second lateral side in a lateral direction, and extending from a superior side to an inferior side in a vertical direction;
   the unitary expandable body being defined by an inferior portion comprising an inferior endplate configured to contact an inferior vertebrae, and a superior portion comprising a superior endplate configured to contact a superior vertebrae, the inferior portion being connected to the superior portion adjacent the distal side of the body at a connection region;
   a set screw rotatably supported by a threaded aperture formed within the proximal side of the body and rotatable in a clockwise direction and counterclockwise direction around a rotation axis; and
   a plug disposed adjacent to and in contact with the set screw, the plug having a first inclined surface facing the distal side of the body,
   wherein:
   the superior portion comprises a first inclined ramp disposed on an interior surface thereof and facing the first inclined surface of the plug,
   the set screw is movable in the longitudinal direction towards the distal side of the body upon rotation of the set screw along the rotation axis, and
   movement of the set screw in the longitudinal direction towards the distal side of the body urges the first inclined surface of the plug against the first inclined ramp thereby moving the body into an expanded position by increasing a vertical distance between the superior portion and inferior portion of the body.

2. The unibody implant of claim 1, wherein the connection region is configured to function as a hinge that undergoes an elastic deformation in the expanded position.

3. The unibody implant of claim 1, wherein the inferior portion comprises the threaded aperture rotatably supporting the set screw and a plug cavity housing the plug.

4. The unibody implant of claim 1, wherein the first inclined surface is a planar surface.

5. The unibody implant of claim 1, wherein:
the inferior portion is connected to the superior portion at the distal side and the distal side is elastically deformable,
the first lateral side comprises a first slit formed as a first discontinuity between the inferior portion and the superior portion, and
the second lateral side comprises a second slit formed as a second discontinuity between the inferior portion and the superior portion.

6. The unibody implant of claim 5, wherein the first discontinuity comprises a first generally teardrop-shaped cutout proximate the distal side and the second discontinuity comprises a second generally teardrop-shaped cutout proximate the distal side.

7. The unibody implant of claim 5, wherein:
the proximal side comprises a third slit formed as a third discontinuity between the inferior portion and the superior portion,
the first slit intersects with the third slit adjacent an inferior surface of the inferior portion, and
the second slit intersects with the third slit adjacent a superior surface of the superior portion.

8. The unibody implant of claim 7, wherein the first slit and second slit comprise an undulating pattern, respectively.

9. The unibody implant of claim 1, wherein:
the inferior portion is connected to the superior portion at the distal side and the distal side is elastically deformable,
the first lateral side comprises a first slit formed as a first discontinuity between the inferior portion and the superior portion,
the second lateral side comprises a second slit formed as a second discontinuity between the inferior portion and the superior portion,
the proximal side comprises a third slit formed as a third discontinuity between the inferior portion and the superior portion,
the first slit connects to the third slit adjacent an inferior surface of the inferior portion, and
the second slit connects to the third slit adjacent a superior surface of the superior portion.

10. The unibody implant of claim 1, wherein:
the plug comprises a stabilizing element extending from an upper portion of the plug towards the proximal side of the body, and
an underside of the stabilizing element directly contacts an upper surface of the inferior portion.

11. The unibody implant of claim 10, wherein in an expanded position compressive forces applied to the superior portion are transferred to the inferior portion via the first inclined surface of the plug and the stabilizing element of the plug.

12. The unibody implant of claim 10, wherein: the inferior portion comprises the threaded aperture rotatably supporting the set screw, an upper portion of the threaded aperture is discontinuous, and the plug extends through the upper portion of the threaded aperture.

13. The unibody implant of claim 12, wherein the stabilizing element comprises a planar surface that extends over the upper portion of the threaded aperture.

14. The unibody implant of claim 1, wherein the inferior portion comprises a first bone screw aperture extending from a first vertical surface of the inferior portion and through a bottom surface of the inferior portion, the first bone screw aperture defining a first bone screw trajectory projecting towards the distal side that is inclined with respect to the bottom surface of the inferior portion.

15. The unibody implant of claim 14, wherein the superior portion comprises a second bone screw aperture extending from a second vertical surface of the superior portion and through a top surface of the superior portion, the second bone screw aperture defining a second bone screw trajectory projecting towards the distal side that is inclined with respect to the top surface of the superior portion.

16. The unibody implant of claim 1, wherein the set screw comprises a first hollow interior and the plug comprises a second hollow interior.

17. The unibody implant of claim 1, wherein the plug comprises a cylindrical portion having a center point and the rotation axis of the set screw is coaxially aligned with the center point of the plug.

18. The unibody implant of claim 1, wherein the plug comprises a cylindrical portion having a hollow center and the rotation axis of the set screw is coaxially aligned with the hollow center of the plug.

19. A method for expanding a unibody implant, comprising:
providing a unibody implant movable between a contracted position and an expanded position, comprising:
a unitary expandable body extending from a proximal side to a distal side in a longitudinal direction, extending from a first lateral side to a second lateral side in a lateral direction, and extending from a superior side to an inferior side in a vertical direction;
the unitary expandable body being defined by an inferior portion comprising an inferior endplate configured to contact an inferior vertebrae and a superior portion comprising a superior endplate configured to contact a superior vertebrae, the inferior portion being connected to the superior portion adjacent the distal side of the body at a connection region;
a set screw rotatably supported by a threaded aperture formed within the proximal side of the body and rotatable in a clockwise direction and counterclockwise direction around a rotation axis; and
a plug disposed adjacent to and in contact with the set screw, the plug having a first inclined surface facing the distal side of the body,
wherein:
the superior portion comprises a first inclined ramp disposed on an interior surface thereof and facing the first inclined surface of the plug,
the set screw is movable in the longitudinal direction towards the distal side of the body upon rotation of the set screw along the rotation axis,
movement of the set screw in the longitudinal direction towards the distal side of the body urges the first inclined surface of the plug against the first inclined ramp thereby increasing a vertical distance of the body between the superior portion and inferior portion of the body, and
rotating the set screw such that it linearly translates from the proximal side towards the distal side of the body;
pushing the plug, by the set screw, towards the distal side of the body; and
urging, by the plug, the first inclined ramp of the superior portion up and away from the inferior portion such that the connection region undergoes an elastic deformation and the unibody implant moves from the contracted position to the expanded position.

20. The method of claim 19, comprising:
maintaining the unibody implant in the expanded position; and
transferring compressive forces of adjacent vertebrae between the superior portion and inferior portion via the first inclined ramp of the superior portion through the first inclined surface of the plug and a stabilizing feature of the plug that directly contacts an upper surface of the inferior portion.

* * * * *